United States Patent [19]

Wollin

[11] Patent Number: 6,166,540
[45] Date of Patent: Dec. 26, 2000

[54] METHOD OF RESISTIVITY WELL LOGGING UTILIZING NUCLEAR MAGNETIC RESONANCE

[75] Inventor: Ernest Wollin, Leesburg, Fla.

[73] Assignee: Wollin Ventures, Inc., Leesburg, Fla.

[21] Appl. No.: 08/885,925

[22] Filed: Jun. 30, 1997

[51] Int. Cl.[7] .................................................. G01V 3/00
[52] U.S. Cl. .......................... 324/300; 324/303; 324/307
[58] Field of Search .................................. 324/300, 303, 324/307, 318

[56] References Cited

U.S. PATENT DOCUMENTS

| | | | |
|---|---|---|---|
| 4,451,789 | 5/1984 | Meador | 324/338 |
| 4,639,671 | 1/1987 | Macovski | 324/309 |
| 4,652,828 | 3/1987 | Kenyon et al. | 324/338 |
| 4,730,161 | 3/1988 | Cox et al. | 324/338 |
| 4,769,606 | 9/1988 | Vinegar et al. | 324/366 |
| 4,774,471 | 9/1988 | Sims et al. | 324/341 |
| 4,780,679 | 10/1988 | Kenyon et al. | 324/338 |
| 4,786,873 | 11/1988 | Sherman | 324/323 |
| 4,933,638 | 6/1990 | Kenyon et al. | 324/303 |
| 5,059,907 | 10/1991 | Sherman | 324/323 |
| 5,162,740 | 11/1992 | Jewell | 324/347 |
| 5,187,661 | 2/1993 | Sinclair | 364/422 |
| 5,200,699 | 4/1993 | Baldwin et al. | 324/303 |
| 5,210,495 | 5/1993 | Hapashy et al. | 324/338 |
| 5,212,447 | 5/1993 | Paltiel | 324/300 |
| 5,233,522 | 8/1993 | Sinclair | 364/422 |
| 5,280,243 | 1/1994 | Miller | 324/303 |
| 5,289,124 | 2/1994 | Jerosch-Herold et al. | 324/303 |
| 5,291,137 | 3/1994 | Freedman | 324/303 |
| 5,309,098 | 5/1994 | Coates et al. | 324/303 |
| 5,332,967 | 7/1994 | Shporer | 324/303 |
| 5,363,041 | 11/1994 | Sezginer | 324/303 |
| 5,367,262 | 11/1994 | Manning | 324/341 |
| 5,376,884 | 12/1994 | Sezginer | 324/303 |
| 5,381,092 | 1/1995 | Freedman | 324/303 |
| 5,387,865 | 2/1995 | Jerosch-Herold et al. | 324/303 |
| 5,389,877 | 2/1995 | Sezginer et al. | 324/303 |
| 5,389,881 | 2/1995 | Bittar et al. | 324/338 |
| 5,412,320 | 5/1995 | Coates | 324/303 |
| 5,412,322 | 5/1995 | Wollin | 324/318 |

(List continued on next page.)

OTHER PUBLICATIONS

Stejskal, E.O., et al., "Spin Diffusion Measurements: Spin Echoes in the Presence of a Time–Dependent Field Gradient", *The Journal of Chemical Physics,* vol. 42, No. 1, Jan. 1, 1965, pp. 288–292.

Bassiouni, Z. "Theory, Measurement, and Interpretation of Well Logs," Society of Petroleum Engineers, Richardson, Texas, 1994, Chapt. 5, pp. 92–95.

Bassiouni, Z. "Theory, Measurement, and Interpretation of Well Logs," Society of Petroleum Engineers, vol. 14, Richardson, Texas, 1994, pp. 252–253, 276.

Burington, R.S. "Handbook of Mathematical Tables and Formulas", HAndbook Publishers, Inc., Sandusky, Ohio, 1949, n. 202, p. 73.

Janke, E., and Emde, F. Sommerfeld: Math. Ann. 47,335, 1986, cited in Tables of Functions Janmke and Emde, 4th ed. Dover.

Slichter, C.P. "Principles of Magnetic Resonance," 3rd ed., Springer–Verlag, Berlin, 1989, Appendix G.

Slichter, C.P. "Principles of Magnetic Resonance," 3rd ed., Springer–Verlag, Berlin, 1989, eq 7.376, 7.377, p. 358.

Smythe, W.R. "Static and Dynamic Electricity," McGraw–Hill Book Company, New York, 1950, Chap. XI, pp. 390–397.

Stejskal, E.O. J. Chem. Phus., vol. 43, n. 10, Nov. 15, 1965, pp. 3597–3603.

*Primary Examiner*—Jay Patidar
*Assistant Examiner*—Brij B. Shrivastav
*Attorney, Agent, or Firm*—Foley & Lardner

[57] ABSTRACT

A method for determining petrophysical properties of geological structures using nuclear magnetic resonance utilizes a well logging apparatus and estimates resistivity in the formation surrounding a borehole by measuring current field strength and distribution.

23 Claims, 12 Drawing Sheets

U.S. PATENT DOCUMENTS

| | | | |
|---|---|---|---|
| 5,428,293 | 6/1995 | Sinclair et al. | 324/339 |
| 5,432,446 | 7/1995 | MacInnis et al. | 324/303 |
| 5,442,294 | 8/1995 | Rorden | 324/339 |
| 5,451,873 | 9/1995 | Freedman et al. | 324/303 |
| 5,463,320 | 10/1995 | Bonner et al. | 324/366 |
| 5,463,549 | 10/1995 | Dussan et al. | 364/422 |
| 5,469,062 | 11/1995 | Meyer, Jr. | 324/338 |
| 5,486,761 | 1/1996 | Sezginer | 324/303 |
| 5,486,762 | 1/1996 | Freedman et al. | 324/303 |
| 5,497,087 | 3/1996 | Vinegar et al. | 324/303 |
| 5,498,960 | 3/1996 | Vinegar et al. | 324/303 |
| 5,517,115 | 5/1996 | Prammer | 324/303 |
| 5,525,904 | 6/1996 | Hanley et al. | 324/300 |
| 5,532,593 | 7/1996 | Maneval et al. | |
| 5,539,309 | 7/1996 | Van Wyk et al. | 324/307 |
| 5,550,473 | 8/1996 | Klein | 324/338 |
| 5,557,200 | 9/1996 | Coates | 324/303 |
| 5,557,201 | 9/1996 | Kleinberg et al. | 324/303 |
| 5,565,775 | 10/1996 | Stallmach et al. | 324/303 |
| 5,574,371 | 11/1996 | Tabanou et al. | 324/324 |
| 5,585,720 | 12/1996 | Edwards | 324/309 |
| 5,585,722 | 12/1996 | Hosoki et al. | 324/318 |
| 5,585,727 | 12/1996 | Fanini et al. | 324/339 |
| 5,596,274 | 1/1997 | Sezginer | 324/303 |
| 5,696,448 | 12/1997 | Coates et al. | 324/303 |
| 5,936,405 | 8/1999 | Prammer et al. | 324/303 |

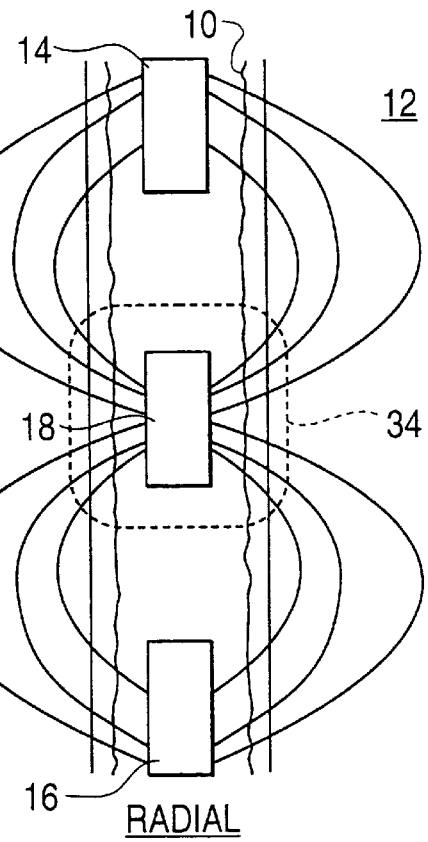
FIG. 8  RADIAL
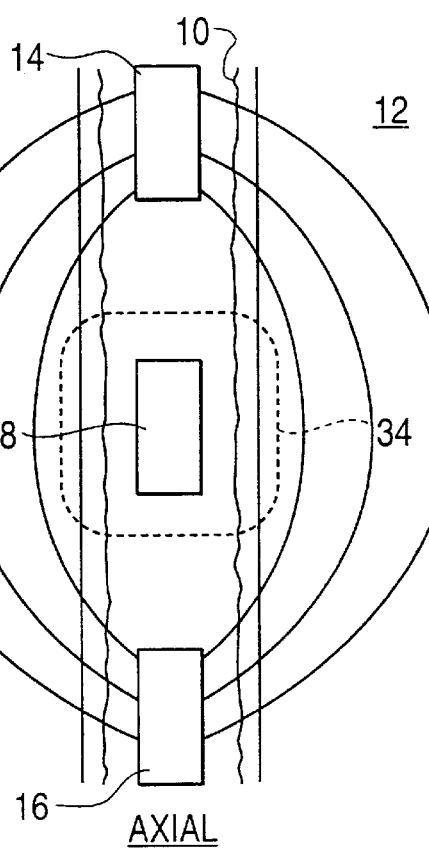
FIG. 9  AXIAL

RADIAL

AXIAL

FIG. 13a

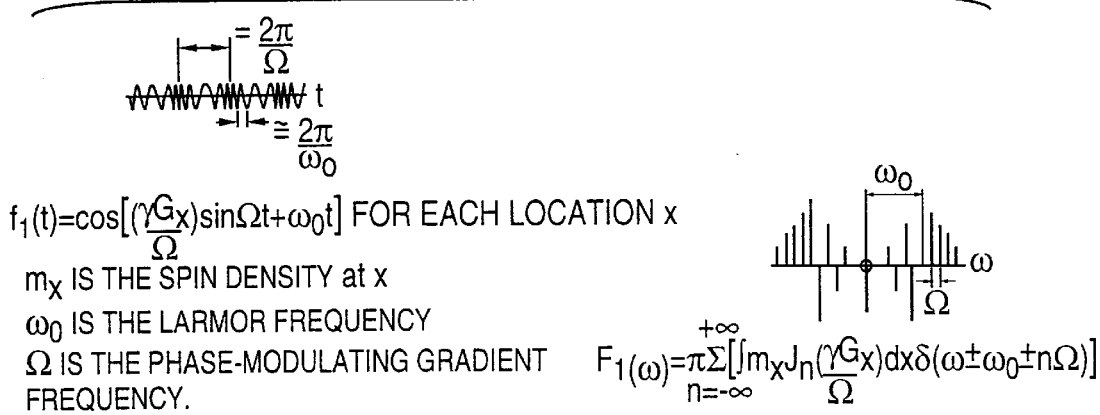

$f_1(t) = \cos[(\frac{\gamma G}{\Omega}x)\sin\Omega t + \omega_0 t]$ FOR EACH LOCATION x $m_x$ IS THE SPIN DENSITY at x
$\omega_0$ IS THE LARMOR FREQUENCY
$\Omega$ IS THE PHASE-MODULATING GRADIENT FREQUENCY.

$F_1(\omega) = \pi \sum_{n=-\infty}^{+\infty} [\int m_x J_n(\frac{\gamma G}{\Omega}x) dx \delta(\omega \pm \omega_0 \pm n\Omega)]$

FIG. 13b

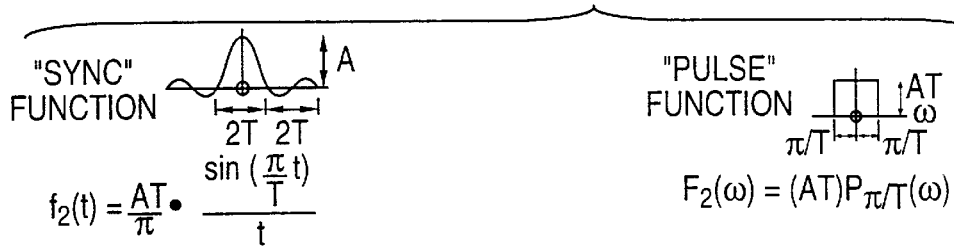

"SYNC" FUNCTION $f_2(t) = \frac{AT}{\pi} \cdot \frac{\sin(\frac{\pi}{T}t)}{t}$

"PULSE" FUNCTION $F_2(\omega) = (AT)P_{\pi/T}(\omega)$

FIG. 13c

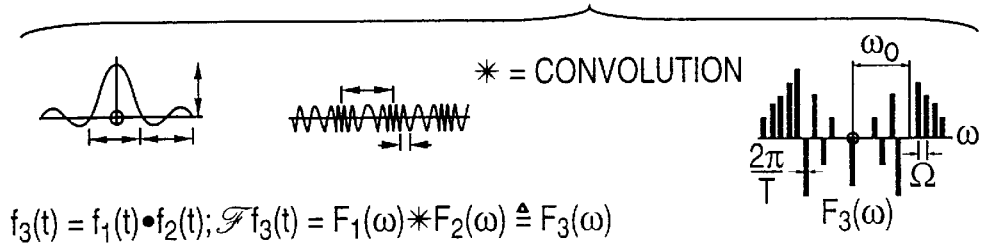

$* =$ CONVOLUTION $f_3(t) = f_1(t) \cdot f_2(t); \mathscr{F} f_3(t) = F_1(\omega) * F_2(\omega) \triangleq F_3(\omega)$ $\mathscr{F} f_4(t) \cdot f_3(t) = F_4(\omega) * F_3(\omega) = F_6(\omega)$ $f_7(t) \triangleq f_5(t)f_3(t)$ $\mathscr{F} f_5(t) \cdot f_3(t) = F_5(\omega) * F_3(\omega) = F_7(\omega)$ $\frac{1}{t_0} \int_0^{t_0} \mathscr{F}^{-1}[F_{9C}(\omega) * F_8(\omega) + F_{10S}(\omega) * F_8(\omega)] dt = \int m_x J_1(\frac{\gamma G}{\Omega}x) dx \triangleq \hat{V}_1$ $\frac{1}{t_0} \int_0^{t_0} \mathscr{F}^{-1}[F_{ncos}(\omega) * F_8(\omega) + F_{nsin}(\omega) * F_8(\omega)] dt = \int m_x J_n(\frac{\gamma G}{\Omega}x) dx \triangleq \hat{V}_n$

METHOD OF RESISTIVITY WELL LOGGING UTILIZING NUCLEAR MAGNETIC RESONANCE

BACKGROUND OF THE INVENTION

1. Field of the Invention

The present invention relates to the determination of petrophysical properties of geologic structures and, more particularly, to resistivity well logging using nuclear magnetic resonance.

2. Description of Related Art

Measurement of rock formation resistivity by electrode well logging is an established technique for estimating the petrophysical properties of the formation surrounding a "conducting" borehole. Numerous devices employing various arrays of electrodes are, or have been, in use since the first resistivity log was recorded in Pechelbronn, France in 1927 by Conrad Schlumberger. All such devices have in common the production of a current density field in the formation by an electric power source and the mapping of potential differences along the borehole or the mapping of electrode potentials required to maintain a specified current distribution in the borehole. See, Bassiouni, Zaki, "Theory, Measurement, and Interpretation of Well Logs"; Society of Petroleum Engineers; Richardson, Tex., 1994, Chapter 5. All prior art electrode devices measure voltages or currents at the internal surface of the borehole. Subsequent analysis is then performed to loosely correlate these borehole measurements with some of the petrophysical characteristics of the surrounding formation.

Induction tools were introduced in the mid-1940's to estimate resistivity in non-conducting boreholes. These devices magnetically induce a current flux in the formation surrounding the borehole, which formation acts as a lossy distributed mutual inductance between two or more measuring inductances. Exemplary of such a device is that shown and described in U.S. Pat. No. 5,428,293 to Sinclair et al.

While such electrode and induction tools have been widely used over the years, they have not proven to be fully satisfactory because they provide only gross approximations of resistivity distributors. Attempts have been made to overcome some of the disadvantages of both induction and of direct contact electrode current and voltage measurement devices by using other logging techniques.

Nuclear magnetic resonance devices measure other related characteristics of the rock formation surrounding a borehole. Nuclear magnetic resonance devices have been applied, for example, to measure such geophysical properties as porosity, pore size distribution, bulk fluid volume, and irreducible bound fluid volume of geological formations surrounding a borehole. Applications of this type are exemplified in U.S. Pat. No. 4,933,638 to Kenyon; No. 5,212,447 to Paltiel; No. 5,280,243 to Miller; No. 5,389,877 to Sezginer; No. 5,412,320 to Coates; No. 5,432,446 to Macinnis; No. 5,486,761 to Freedman; and No. 5,557,200 to Coates.

Representative of magnetic resonance logging tools is a device marketed under the mark MRIL by Numar Corporation. The Numar device has a sensitive volume approximating a thin cylinder 24 inches in height, 16 inches in diameter, and of one millimeter slice thickness surrounding a borehole of 8 to 12 inches diameter. This device permits measurements to be made peripheral to the borehole mud, the mudcake on the borehole wall and often to the flushed zone and the transition zone, yielding an improved estimate of the properties of the uninvaded formation surrounding the borehole relatively free of borehole effect. See, Bassiouni; op. cit. p. 71, 72.

While the value of concordant resistivity data has long been appreciated, and while the application of nuclear magnetic resonance techniques to the derivation of reasonably accurate information on pore size, bulk fluid volume and similar physical characteristics of geologic formations has been recognized, the advantages attendant to the simultaneous use of nuclear magnetic resonance for additionally determining the resistivity of geologic structures surrounding a borehole have not heretofore been realized.

SUMMARY OF THE INVENTION

Accordingly, it is an object of the present invention to provide, in an embodiment a resistivity well logging method utilizing nuclear magnetic resonance.

A further object of the present invention is to provide, in an embodiment, a method for estimating resistivity in a formation surrounding a borehole. The method includes providing a magnetic resonance well logging tool with a Faraday shield, and placing the magnetic resonance well logging tool and Faraday shield in the borehole and capacitively coupling the same with the formation surrounding the borehole. The method further includes energizing the formation surrounding the borehole, and selectively applying phase modulating voltages to the Faraday shield and an upper and a lower coupling member to establish current fields (i) in axial and radial directions, respectively, in the formation surrounding the borehole, and/or (ii) in at least one of axial and radial directions in the formation surrounding the borehole. The method further includes measuring the current strength and distribution of the current fields by detecting phase modulation of spins of materials in a sensitive volume.

It is also an object of the present invention to provide, in an embodiment, a method for determining resistivity in a formation surrounding a borehole. The method includes capacitively coupling a phase-modulating current to the formation by placing first, second, and third spaced coupling members in the borehole and selectively applying low frequency power signals to the first and second coupling members and to the second and third coupling members, respectively. The method further includes placing a magnetic resonance well logging tool in the borehole in proximity to the second coupling member to produce a magnetic resonance sensitive volume around the tool, and detecting phase modulation of spins in the sensitive volume to derive data representative of the resistivity of materials in the formation.

Another object of the present invention is to provide, in an embodiment, another method for determining resistivity in a formation surrounding a borehole. The method includes placing capacitive coupling members above and below a center capacitive coupling member containing a magnetic resonance well logging tool, and selectively establishing current fields (i) in axial and radial directions, respectively, in a sensitive region around the tool, and/or (ii) in at least one of axial and radial directions in a sensitive region around the tool. The method further includes determining resistivity in the sensitive region around the tool utilizing the current fields.

It is yet a further object of the present invention to provide, in an embodiment, yet another method for determining resistivity in a formation surrounding a borehole.

The method includes placing a magnetic resonance well logging tool in the borehole and energizing the tool to produce a magnetic resonance sensitive volume thereabout. The method further includes selectively measuring current flow in the formation (i) both perpendicular to and parallel to the borehole axis within and adjacent to the sensitive volume, and/or (ii) wherein the current flow is at least one of perpendicular to and parallel to the borehole axis within and adjacent to the sensitive volume. The method further includes determining resistivity in the formation utilizing the current flow which is measured.

Another object of the present invention is to provide, in an embodiment, a further method for determining resistivity in a formation surrounding a borehole. The method includes placing a magnetic resonance well logging tool having a Faraday shield in the borehole and capacitively coupling the same with the formation surrounding the borehole. The method further includes placing upper and lower coupling members in the borehole above and below the Faraday shield of the magnetic resonance well logging tool, respectively, and capacitively coupling the same with the formation surrounding the borehole. The method further includes selectively applying voltages to the Faraday shield and the upper and lower coupling members to establish current fields (i) in axial and radial directions, respectively, in the formation, and/or (ii) in at least one of axial and radial directions in the formation. The method further includes measuring the resulting nuclear magnetic resonance signals to determine resistivity within the formation.

A further object of the present invention is to provide, in an embodiment, a method for measuring diffusion coefficient and spin relaxation time in a nuclear magnetic resonance well logging system. The method includes placing a nuclear magnetic resonance well logging device in a borehole having a surrounding formation, and energizing the nuclear magnetic resonance well logging device to generate a phase modulating current at a selected frequency and with a predetermined magnetic resonance pulse interval. The method further includes varying the intensity of the phase modulating current and the frequency and magnetic resonance pulse interval so as to change the amplitude of a magnetic resonance signal, and determining a value for diffusion coefficient and a value for spin relaxation time utilizing the magnetic resonance signal.

The methodology according an embodiment of to the present invention of combining magnetic resonance logging with resistivity well logging may be used with any suitable magnetic resonance well logging tool, but is particularly well suited for use with magnetic resonance tools in which magnetic field gradients are produced by the application of time-varying electric fields as disclosed in applicant's U.S. Pat. No. 5,412,322, entitled "Apparatus and Method for Spatially Ordered Phase Encoding and for Determining Complex Permittivity in Magnetic Resonance by Using Superimposed Time-Varying Electric Fields," which is incorporated herein by reference.

The data generated by the magnetic resonance tool in accordance with an embodiment of this invention may be obtained by using any suitable output recovery technique, but is most suitably retrieved by the implementation of techniques of demodulation and detection of phase-modulated magnetic resonance signals, as more fully disclosed herein.

In the implementation of an embodiment of the present invention, electrode arrays supplied by periodic voltage or periodic current sources are placed in either "conducting" or "non-conducting" boreholes and are configured to produce either predominately radial or predominately axial periodic current fields. These fields are used to phase modulate signals produced by spin distributions created by a nuclear magnetic resonance well logging device. Measurements may be made in low conductivity boreholes by capacitively coupling Very Low Frequency currents (e.g. 1–10 KHz) to the conductive formation surrounding the borehole through impedance matching circuits.

A phase-modulated magnetic resonance signal consisting of a line spectrum is created by these current fields which can then be "demodulated" by convolution and cross-correlation with the master radio frequency oscillator frequency $H_1$. Individual sideband "lines" can be "detected" by convolution and cross-correlation with integral multiples of the phase-modulating frequency of the current field, all of which is the radio engineering embodiment of statistically determining the amplitude of low power hidden periodicities in a stationary random process when the frequency of these periodicities is a known integral multiple of a reference signal available from a master oscillator. The central and the peripheral components of apparent formation resistivity $R_a$ may be estimated separately. Spin-spin relaxation $T_2$ and diffusion D may be estimated in the bulk non-surface associated large pore component of formation fluid.

Additional objects, advantages and features of embodiments of the present invention will become apparent to those skilled in the art from the following description of the preferred embodiment when taken in conjunction with the attached appendices and accompanying drawings.

BRIEF DESCRIPTION OF THE DRAWINGS

FIGS. 8 and 9 are diagrammatic views of the upper coupling member, the middle coupling member and magnetic resonance tool, and the lower coupling member showing the current fields established in the radial and axial modes of operation, respectively, of the embodiment of FIG. 1 in accordance with the present invention;

FIGS. 13a–13i are a series of curves showing the signals at various points in the sideband detector of FIG. 1.

DETAILED DESCRIPTION OF THE PREFERRED EMBODIMENTS

Figure 1:
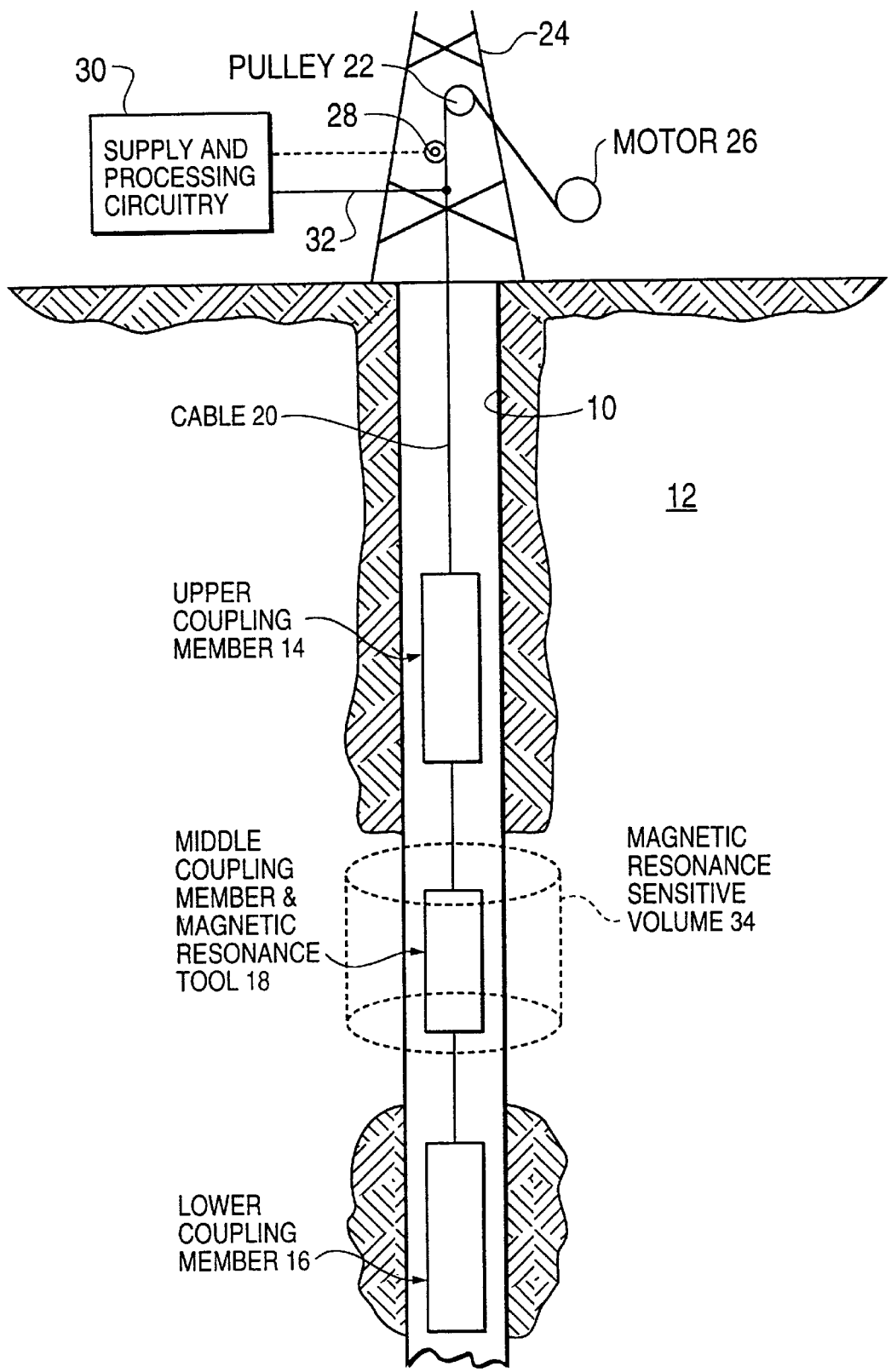
FIG. 1 is a partially pictorial, partially block diagram of a preferred embodiment of a resistivity well logging apparatus using nuclear magnetic resonance in accordance with the present invention.

Referring to FIG. 1, a borehole 10 is shown in a formation 12 of geologic structures, the petrophysical properties of which are to be examined using the apparatus and method of the present invention. Positioned within borehole 10 is a three-part resistivity well logging assembly utilizing nuclear magnetic resonance. The assembly consists of an upper coupling member 14, a lower coupling member 16, and a middle coupling member and magnetic resonance tool 18 positioned therebetween.

The upper coupling member 14, the lower coupling member 16, and the middle coupling member and magnetic resonance tool 18 are suspended in spaced relationship, as illustrated in FIG. 1, on a suitable cable 20. Cable 20 is routed above the borehole 10 over a pulley 22 which is mounted on a suitable support frame 24. The end of the cable 20 is attached to a suitable takeup spool (not shown) mounted on and driven by a motor 26.

The position of the cable 20 within borehole 10 is determined by a position sensing roller 28 or other suitable depth metering device. The cable depth information is fed to electrical supply and processing circuitry 30 containing power source and control equipment and signal processing and recording equipment as will be more fully described below. Supply and processing circuitry 30 is electrically connected to cable 20 by an electrical feed line 32.

In accordance with the present invention, the middle coupling member 18 also contains a magnetic resonance tool which, when energized, establishes a magnetic resonance sensitive volume 34 in the generally cylindrical space surrounding the member 18 as diagrammatically illustrated in FIG. 1.

Figure 2:
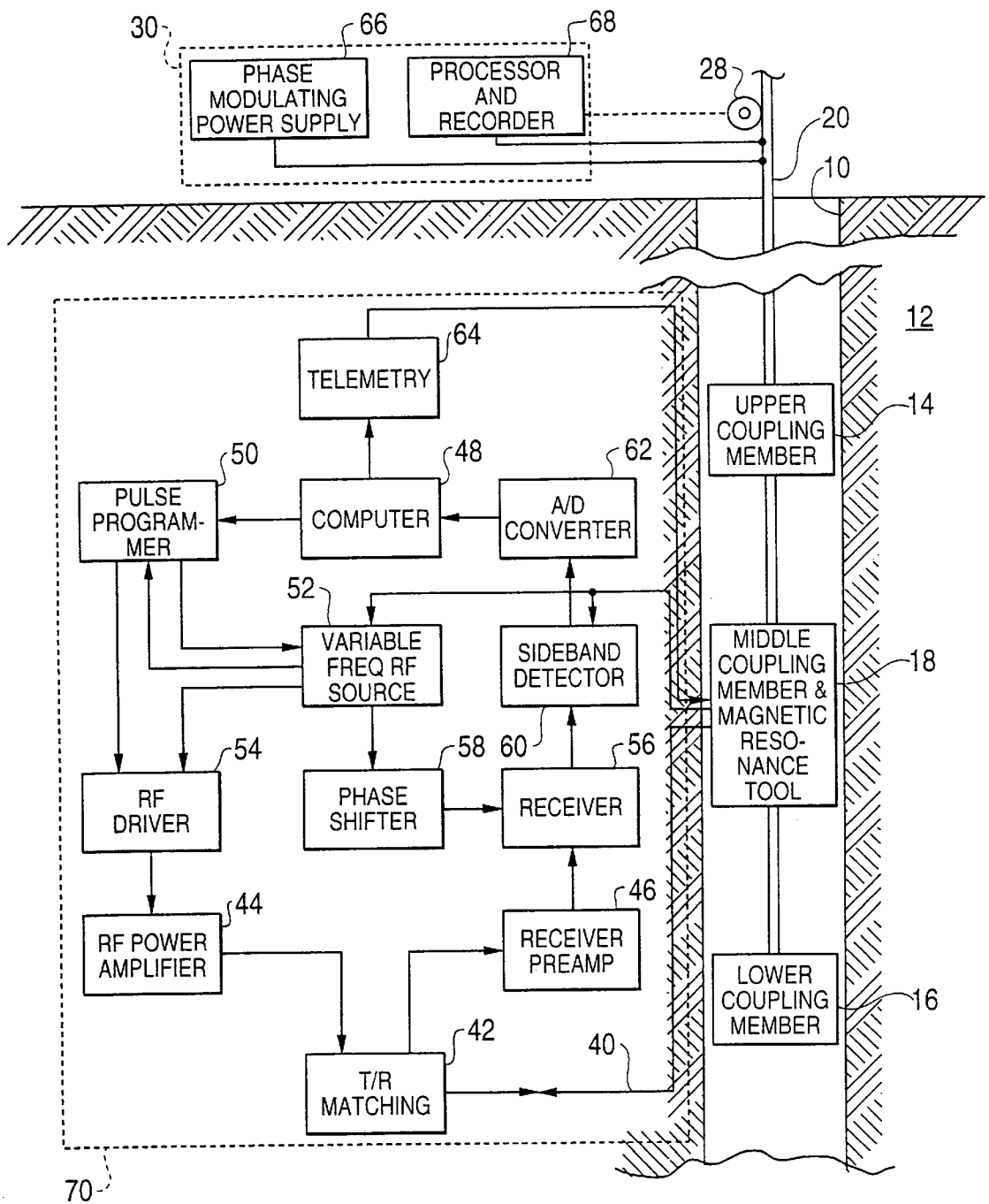
FIG. 2 is a partially pictorial, partially block diagram of the components of the apparatus of FIG. 1 in accordance with the present invention.

FIG. 2 is a partially pictorial and partially block diagram of the components of the apparatus of FIG. 1 in accordance with the present invention. In FIG. 2, the radio frequency antenna of the magnetic resonance tool of middle coupling member 18 is electrically coupled by a line 40 to a transmitter/receiver (T/R) matching circuit 42. The T/R matching circuit 42 typically includes a resonance capacitor, a T/R switch, and both transmit and receive matching circuits. The T/R matching circuit is coupled to an RF power amplifier 44 and to a receiver preamplifier 46.

System control is provided by a computer 48, which provides a control output to a pulse programmer 50. The pulse programmer 50 receives an RF input from a variable frequency RF source 52, which is synchronized with the phase modulating power supply 66 through cable 20, as illustrated. The pulse programmer 50 also controls the operation of an RF driver 54, which receives an input from variable frequency RF source 52 and outputs a signal to RF power amplifier 44.

The output of the RF receiver preamplifier 46 is supplied to an RF receiver 56 which receives an input from a phase shifter 58 in response to a signal received from the variable frequency RF source 52. Receiver 56 is connected to a sideband detector 60 which, in accordance with the present invention, receives a reference signal from power supply 66 through cable 20, demodulates and detects the output of receiver 56 and then supplies the resulting output to an analogue to digital (A/D) converter 62. The output of the A/D Converter 62 is fed to computer 48 which, in turn, provides desired well logging output data to the supply and processing circuitry 30 via a telemetry circuit 64.

Supply and processing circuitry 30, in accordance with the present invention, includes a phase-modulating power supply 66 which supplies "low" frequency electric power down the cable 20 to the coupling members 14, 16 and 18, as will be more fully described hereinbelow, which also can be converted to supply power to the elements contained in block 70. Circuit 30 also includes a processor and recorder 68 which receives the data from telemetry circuit 64 and position sensor 28, processes the same, and records the information for further reference and analysis.

Many of the elements described above may be contained within a housing, diagrammatically shown as block 70, mounted in suitable fashion on, adjacent to or within the middle coupling member and magnetic resonance tool 18. Alternatively, some of the elements contained within block 70 may be contained in separate housings or within the supply and processing circuitry 30 outside the borehole and above ground.

Figure 3:
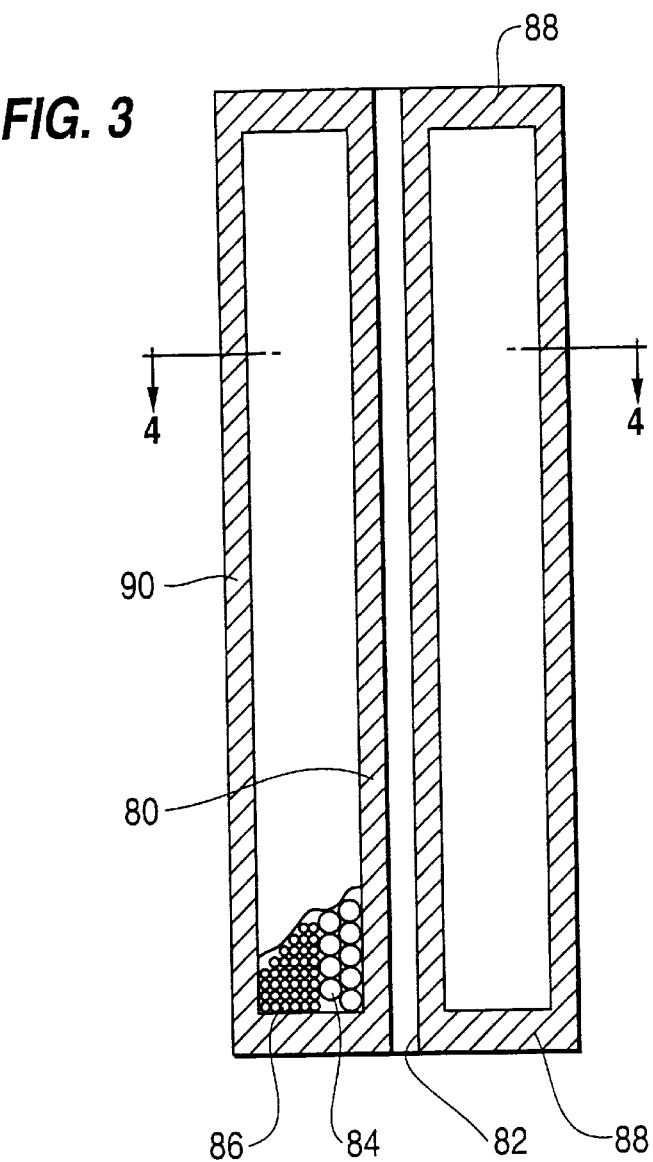
FIG. 3 is a cross-sectional view of a coupling element and integral transformer of the apparatus of FIG. 1.
Figure 4:
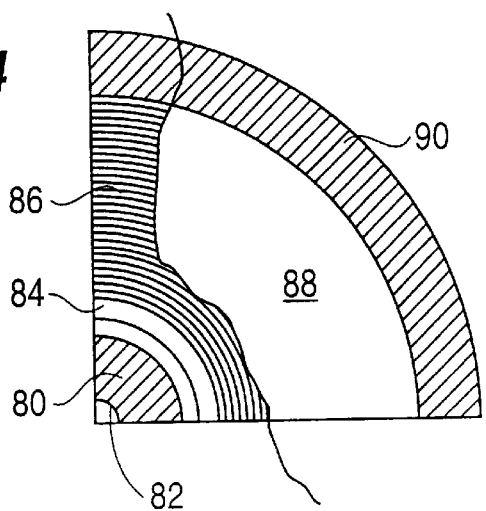
FIG. 4 is a one-quarter cross-sectional view of the coupling element and integral transformer taken along line 4—4 of FIG. 3.

Each of the upper and lower coupling members 14 and 16, respectively, may be constructed in similar fashion in accordance with the present invention. An exemplary configuration for such members is illustrated in more detail in FIGS. 3 and 4.

The coupling members may be constructed of a cylindrical steel tube 80 having an outer radius $r_2$. Tube 80 is provided through its full length with an axial hole 82 having a radius $r_1$. Hole 82 serves as a raceway for cable 20. Wound around tube 80 is a primary winding 84, which has a secondary winding 86 wound concentrically thereover to form a transformer. The ends of tube 80 are provided with generally circular end plates 88 to contain the primary and secondary windings 84 and 86. An outer, generally cylindrical steel pipe 90, having an interior radius $r_3$ and an exterior radius $r_4$, surrounds the entire assembly and is mechanically and electrically interconnected with the tube 80 and each of the end plates 88 to form a self-contained unit.

The following dimensions are provided for each of the upper and lower coupling members, assuming equal flux density in steel: $r_1$=0.25 inches; $r_2$=1.225 inches; $r_3$=2.75 inches; $r_4$=3 inches; and axial length=7 feet. While the configuration described and illustrated in FIGS. 3 and 4 for the upper and lower coupling members 14 and 16 is considered to be most suitable, any other desired configuration capable of providing capacitive or conductive coupling to the interior of the borehole while at the same time providing impedance matching, to bring the entire circuit into zero phase angle unity power factor series resonance, may be employed. To that end, and as will be described more fully below, the transformer contained within each of the upper and lower coupling members 14 and 16, respectively, may be provided with an impedance adjusting coil to assist in achieving zero phase angle unity power factor series resonance.

Figure 5:
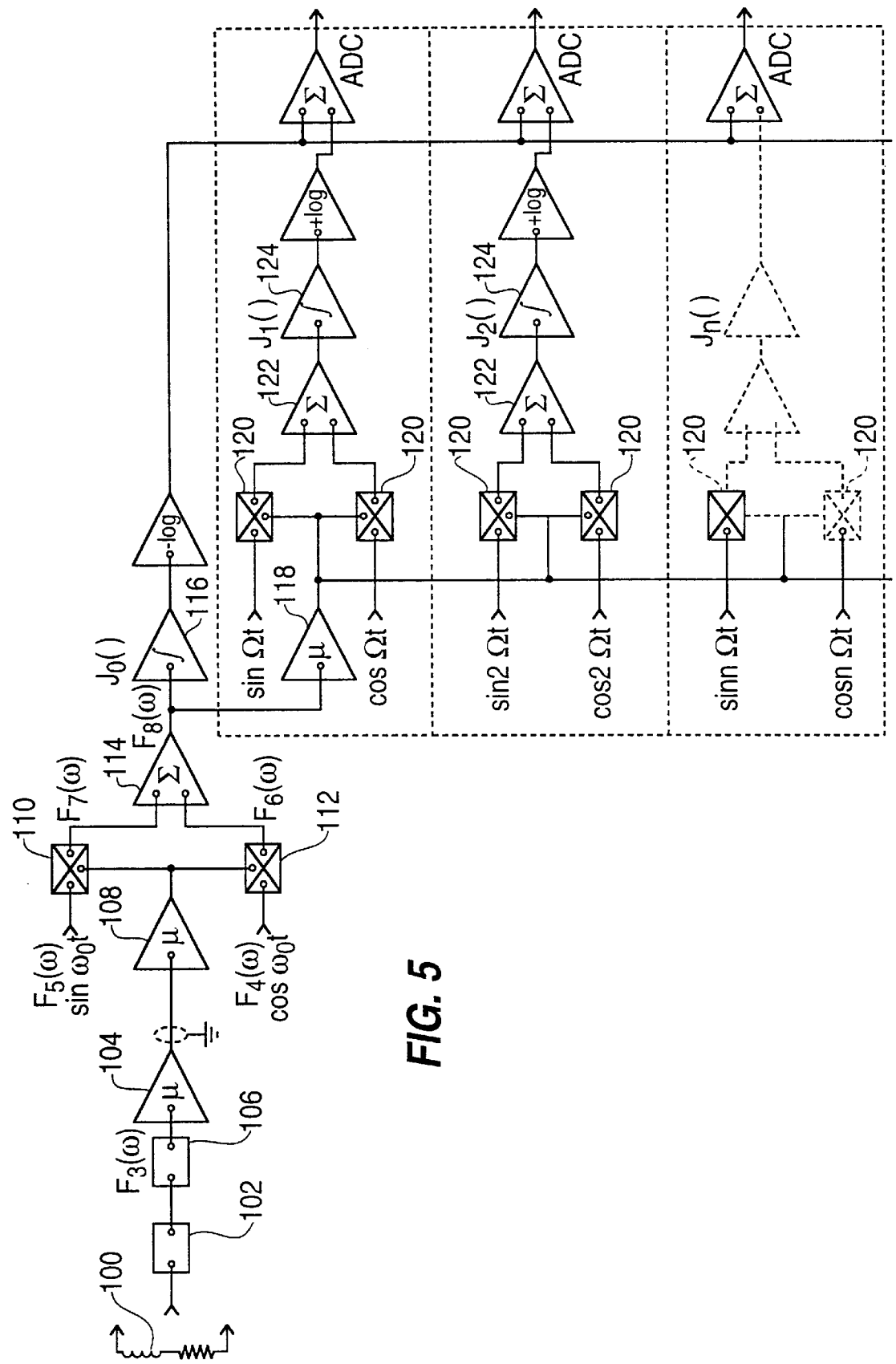
FIG. 5 is a block diagram of the sideband detector of FIG. 2.

A preferred embodiment of sideband detector 60 is shown in FIG. 5. In FIG. 5, antenna 100 of the magnetic resonance tool 18 is coupled to an impedance matching circuit 102, feeding a noise matching preamplifier 104 through a protection circuit 106. The output of the noise matching preamplifier is fed to an RF amplifier 108, the output of which is directed to a double-balanced demodulator 110, 112. The output of the double-balanced demodulator 110, 112 is fed through a summing amplifier 114 to an alternating current integrator 116 and an audio frequency amplifier 118. Each of the demodulators 110 and 112 is supplied by a quadrature output from the magnetic resonance master radio frequency oscillator. The demodulated outputs are then added at summer 114 to provide a cross-correlated input to the integrator 116 (estimating the direct current $J_0(\ )$ term) as well as to a low frequency amplifier 118 that, in turn, feeds additional sets of double-balanced demodulators 120, 121 each of whose added cross-correlated outputs are also summed by summers 122 and integrated by integrators 124, thereby estimating the relative strength of each sideband element of the spectrum, $J_n(\ )$.

Figure 6:
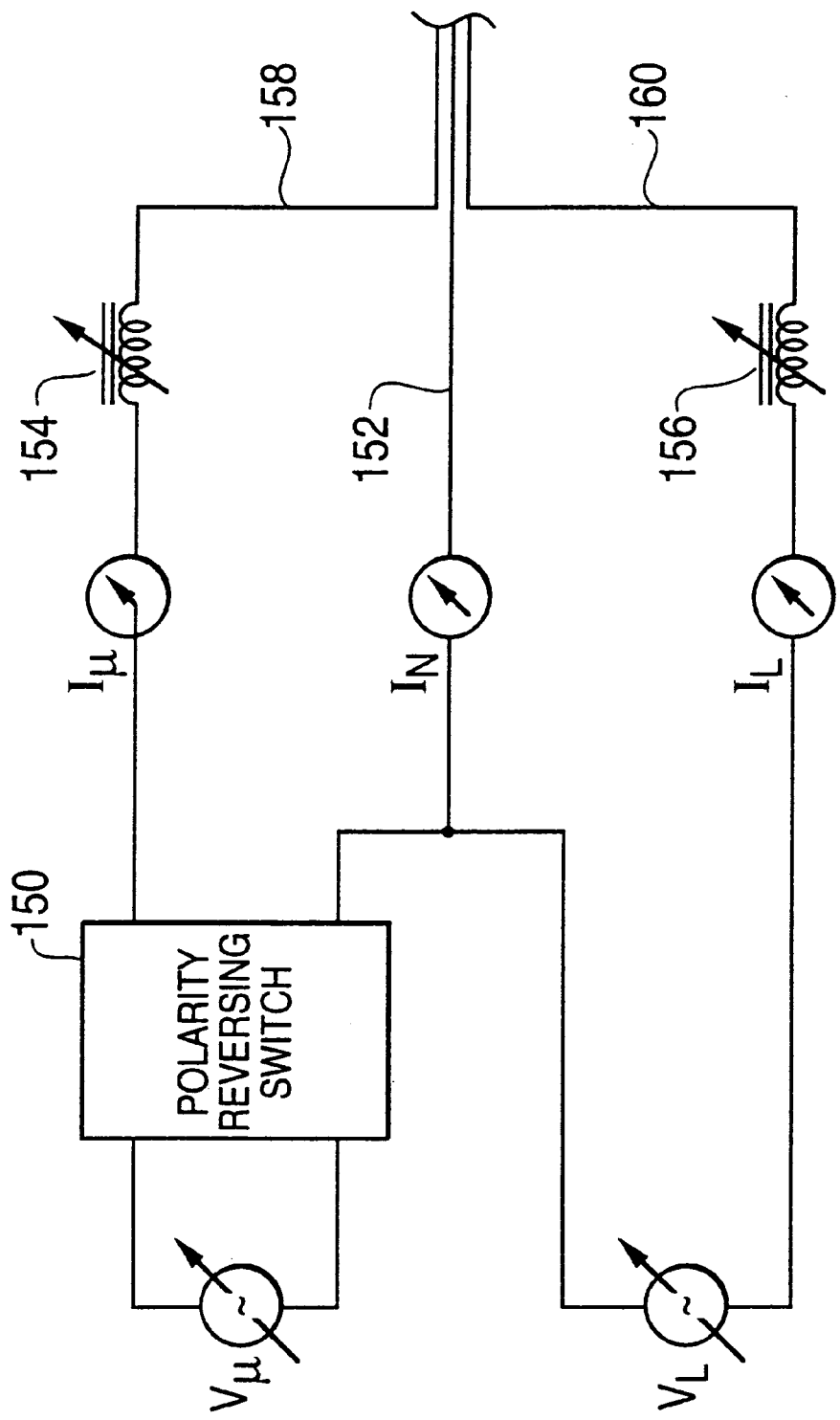
FIG. 6 is a schematic diagram of the phase-modulating power supply of FIG. 2.

Turning to FIG. 6, the phase modulating power supply 66 of the present invention is illustrated in schematic form. The circuit shown in FIG. 6. includes upper and lower high power "low" frequency voltage sources $V_U$ and $V_L$, respectively, each capable of providing, for example, 10 kilowatts of power at a frequency of 10 to 10,000 Hz. The upper voltage source is connected to a polarity reversing switch 150 to enable the output polarity to be selectively reversed depending upon whether operation in the radial or axial modes is desired, as will be described more fully below.

One side of each of the upper and lower voltage sources is coupled through a suitable current measuring device $I_N$ to a neutral cable line 152. The other side of each of the respective upper and lower voltage sources $V_U$ and $V_L$ is coupled through similar current measuring devices $I_U$ and $I_L$ to upper and lower impedance adjusting coils 154 and 156, as shown. The opposite ends of coils 154 and 156 are connected to respective upper and lower cable lines 158 and 160. The cable lines 152, 158 and 160 are electrically insulated from each other and are bundled and fed down the borehole 10 with support cable 20 using suitable electrical cable feed techniques known in the art.

Figure 7:
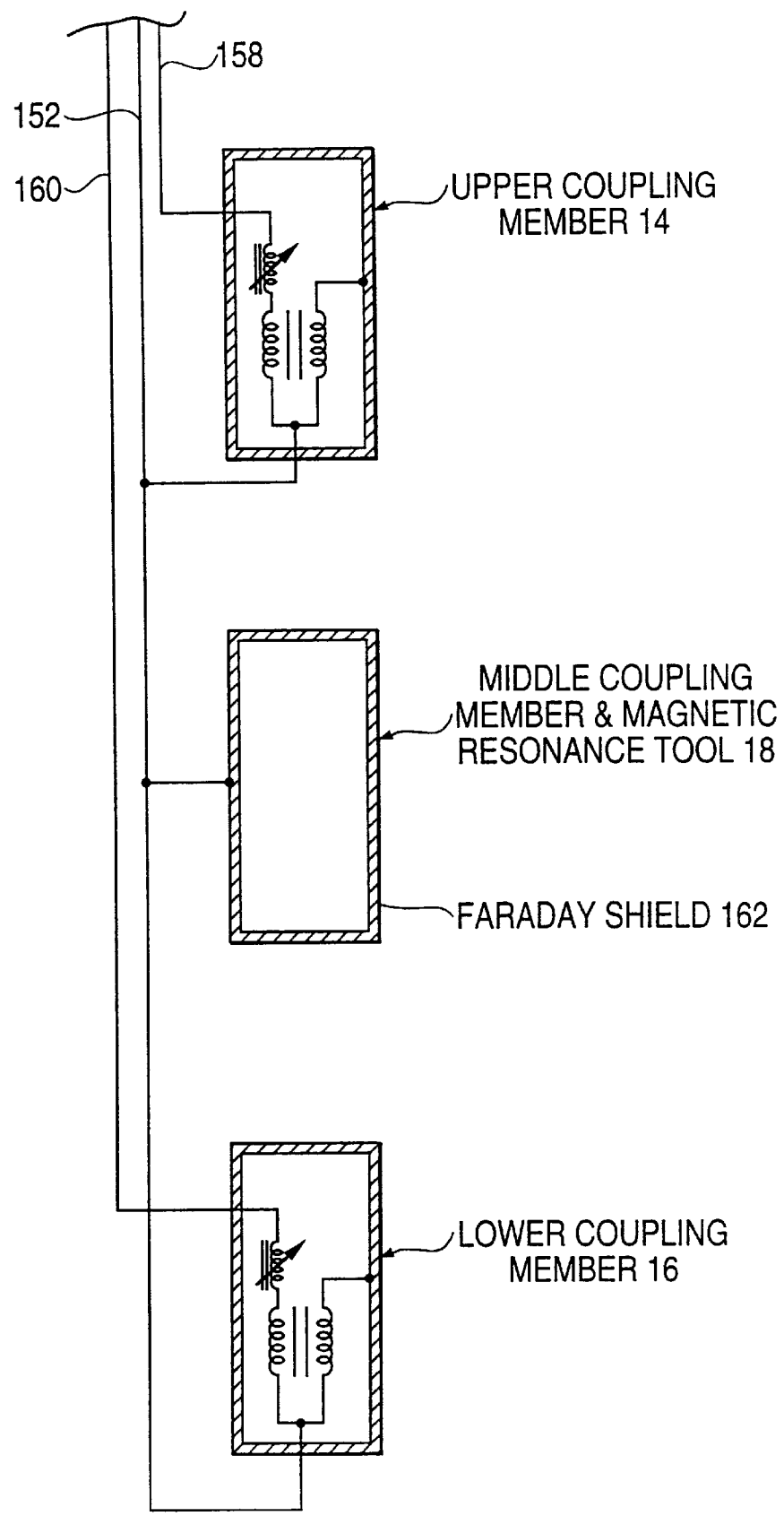
FIG. 7 is a diagrammatic view of the electrical interconnection of the upper coupling member, the lower coupling member, and the middle coupling member and magnetic resonance tool of FIGS. 1 and 2.

Turning now to FIG. 7, cable lines 152, 158 and 160 are fed down the borehole 10 with the upper cable line 158 connected through a suitable matching inductance to the primary coil of the transformer contained within the upper coupling member 14, as illustrated. The opposite end of the primary coil is coupled to one end of the secondary, the opposite end of which is coupled to the steel housing described above and illustrated in FIGS. 3 and 4. The common connection of the primary and secondary windings of the transformer 152 complete the circuit.

In similar manner, the lower cable 160 and the neutral cable 152 are connected to a Faraday shield 162 which surrounds the magnetic resonance tool 18 and forms the middle capacitive coupling member in the triple-coupling array.

FIGS. 8 and 9 illustrate the current field lines created in the borehole and surrounding formation when the three coupling members 14, 16 and 18 are energized in the radial and axial modes, respectively. The radial mode is presented when the polarity reversing switch 150 of the circuit illustrated in FIG. 6 is positioned to provide similar polarization of the upper and lower lines 158 and 160 relative to the neutral line 152. The current fields so created have a predominantly radial component with respect to the sensitive volume of the magnetic resonance device. The effects of the axial current field along the borehole axis cancel (being in opposite directions).

When the upper and lower coupling members are polarized in opposition, a current field is established with current field lines running predominantly parallel to the borehole axis as illustrated in FIG. 9. Only that component of the axially directed current field external to the sensitive volume produces phase modulation and is measured. The effects of any radial components cancel (being equal but opposite above and below a plane transverse to, and containing the midpoint of, the magnetic resonance sensitive volume).

Equivalent circuits for the radial and axial modes of operation are illustrated schematically in FIG. 10 and FIG. 11, respectively, with the resistance calculated and obtained in accordance with the straightforward formulations set forth below.

Figure 12:
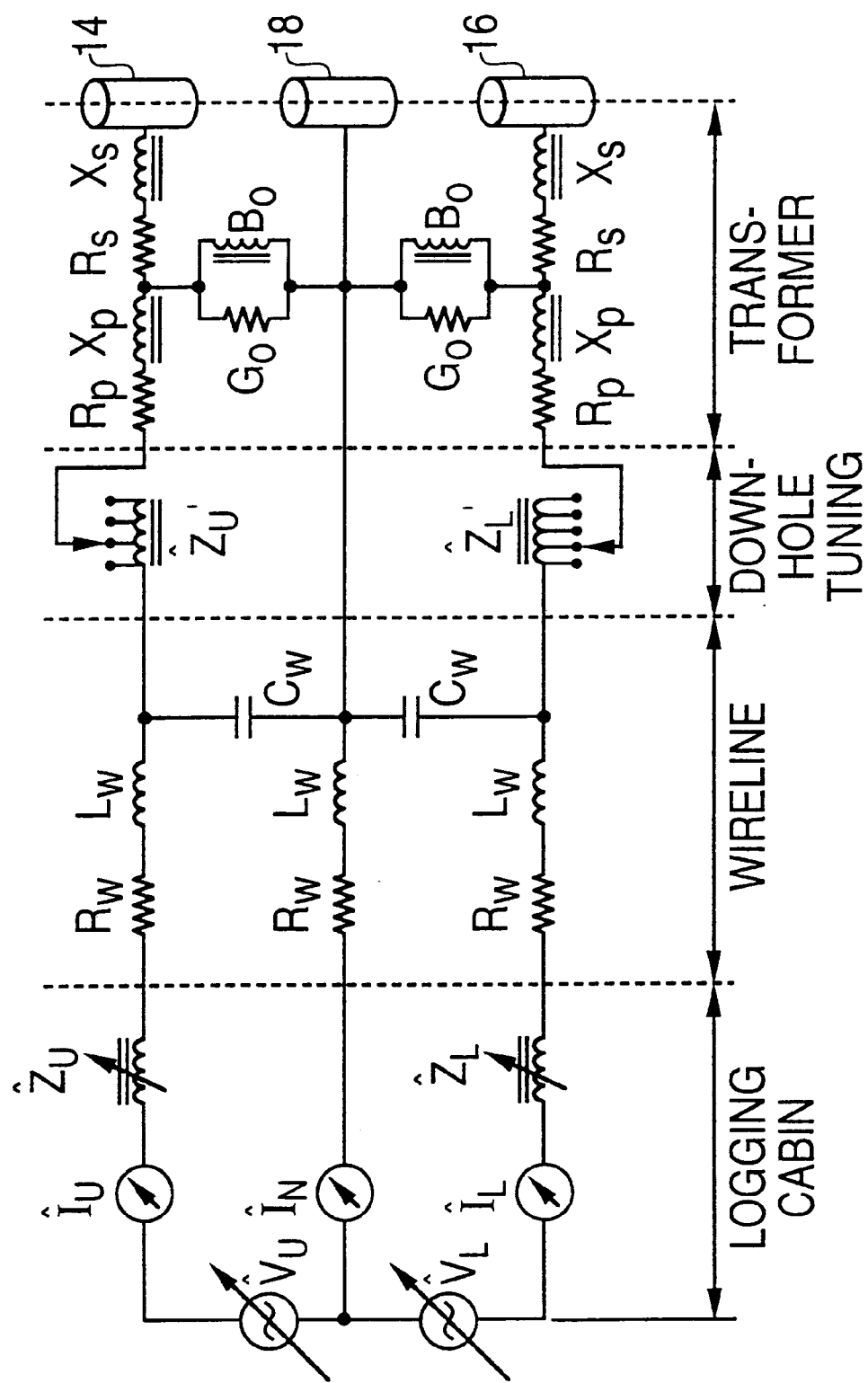
FIG. 12 is a schematic diagram of the equivalent circuit of the phase-modulating power supply, cabling, upper coupling member, middle coupling member and magnetic resonance tool and lower coupling member of FIG. 1.
Figure 13D:
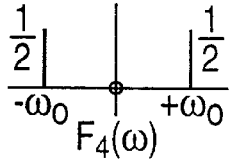
Figure 13E:
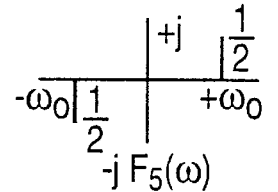
Figure 13F:
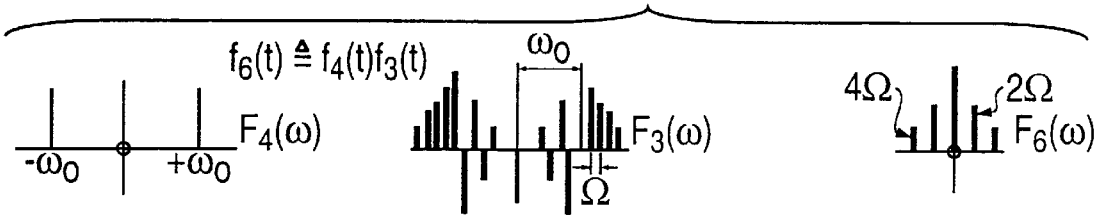
Figure 13G:
Figure 13H:
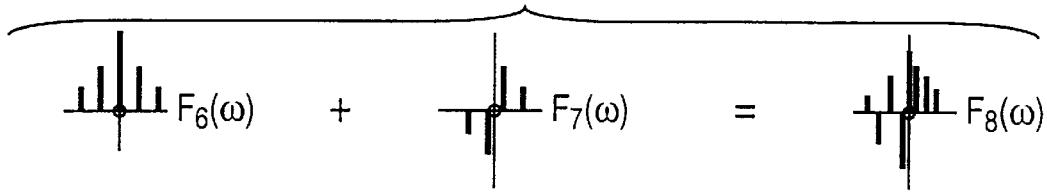
Figure 13I:
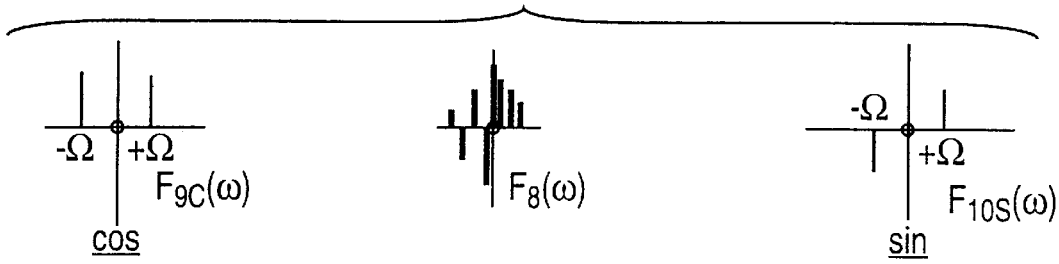

In FIG. 12, a schematic diagram is illustrated showing the equivalent circuit of the overall combination of the phase-modulating power supply circuit 66; the cable feed lines 152, 158 and 160; and the down hole tuning inductances and the transformers contained within the upper and lower coupling members, respectively. From the equivalent circuit, at zero phase angle unity power factor series resonance, accurate calculations can be obtained of apparent resistance values in the geologic formation.

FIGS. 13a–13i illustrate the sidebands produced by the interaction of the phase-modulating electric power and the output of the magnetic resonance tool. The figures also show the formulations used in the derivation of relevant data at different stages of the sideband detection process within the sideband detector 60.

The relationship between the magnetic resonance device depicted as a typical embodiment in applicant's U.S. Pat. No. 5,412,322, incorporated herein by reference, and prior art well logging devices such as the MRIL unit of the Numar Corporation, implies a conformal transformation between the orthogonal rectilinear coordinates, x', y', z' and the orthogonal curvilinear cylindrical coordinates ρ, θ, z.

The Zeeman $H_0$ field is oriented in the $\overline{1}_\theta$ direction in the well logging device and varies in strength radially. A pulsed narrow band radio frequency excitation field $H_1$ is applied perpendicular to the Zeeman $H_0$ field so as to excite only a narrow resonant cylinder of spins coaxial with the borehole. The radius and thickness of this cylinder may be changed by altering the $H_1$ field frequency content.

A gradient field $\overline{G}$ is defined by applicant's U.S. Pat. No. 5,412,322:

$$\rho \overline{G} \triangleq \nabla(\rho h_\theta) = \overline{J} x \rho \overline{1}_\theta$$

$$\overline{J} \equiv \overline{1}_\rho i_\rho + \overline{1}_\theta i_\theta + \overline{k} i_z$$

where $\overline{J}$ is the applied phase modulating current density, assuming circular symmetry in a cylindrical system. (Appendix 1).

A conventional alternating phase Carr-Purcell-Meibom-Gill (CPMG) sequence is utilized to excite (π/2 pulse) and rephase (π pulse) the spins in the sensitive volume. The interval between π pulses 2Tcp can be made short enough (e.g. 1.5–5 ms) to both permit the estimation of formation pore size distribution, by regression analysis of the echo train, and to exclude signals from surface associated fluid, such as in shaly sands.

The echo train is composed of a sum of exponential decays whose time constants are strongly dependent on the surface to volume ratio of each pore size population. Regression analysis then can estimate the relative magnitude of each population of pore sizes permitting separation of the total fluid volume (porosity) into surface associated (bound volume irreducible BVIR) fluid and bulk fluid. Signals associated with fluid in shaly sands are excluded by the initial short Tcp pulse interval, during which time passive diffusion brings surface associated spins close to boundaries which permit spin-lattice relaxation $T_1$ and rapid $T_2$ dephasing, eliminating signals from such spins at a much greater rate than by the dephasing caused by passive diffusion across weaker gradients in bulk fluid.

See, for example, U.S. Pat. No. 5,539,309 to Van Wyk; No. 5,557,200 to Coates; and No. 5,565,775 to Stallmach; and articles by Slichter, C. P. "Principles of Magnetic Resonance", 3rd Edition, 1989, Appendix G; and Stejskal, E. O., J. Chem. Phys., Vol. 43, number 10, Nov. 15, 1965, p. 3597–3603.

For the purpose of this invention, the Tcp interval may be prolonged during all of, or the later part of, the pulse sequence from the 1.5–5 ms, as is used for estimating surface associated fluid volume to estimate bulk fluid volume. The later portion of the echo train then consists of signals from spins associated with bulk fluid, relatively free of surface or diffusion effects, which fluid is composed of an aqueous phase and may also have a hydrocarbon phase.

The spins in bulk fluid are less affected by wall induced susceptibility variations and spin-lattice relaxation and therefore have a narrower bandwidth, producing a more prolonged echo signal, permitting a longer "read" time. This longer signal is preferred for detection of the phase modulation of the spins produced by the time varying gradient created by the time-varying formation current whose frequency is much less than the Larmor frequency, but whose period is much less than the "read" time of the echo. A phase encoding gradient of 10 KHz is compatible with a "carrier" Larmor frequency of 700–1200 KHz.

Both the estimation of surface associated fluid volume (BVIRR) and the measurement of formation current by detecting the resulting phase modulation of the spins in bulk fluid can be accomplished with a single pulse sequence consisting of an initial short Tcp echo train of 1.5–5 ms followed by several longer Tcp intervals.

The interval between pulse sequences $T_r$ (or W wait time) is made long enough to allow relaxation of the hydrocarbon of interest (U.S. Pat. No. 5,497,087 and No. 5,498,960, both to Vinegar) but short enough to permit rapid data acquisition (U.S. Pat. No. 5,309,098 to Coates; and No. 5,486,762 to Freedman).

This invention adds two systems of electrodes in the borehole to pre-existing magnetic resonance well logging devices:

A conductor array (such as a Faraday shield) with electrodes perpendicular to the $E_1$ component of the RF field, arranged coaxial to the borehole and placed around the magnetic resonance device so as not to affect the RF field, creates a current field with a predominately radial component with respect to the sensitive volume of the magnetic resonance device when indifferent electrodes are symmetrically placed within the borehole above and below the magnetic resonance device. Only the radial component of the current field directly perpendicular to the Zeeman $H_0$ field is measured by its effect in producing phase modulation of the magnetic resonance signal. This radial component is measured and separated from the total current flow. The effects of the axial current field along the borehole axis cancel (being in opposite directions). This permits an estimation of the apparent resistance of the borehole profile and of the formation near the sensitive magnetic resonance volume, in a series distribution. (Appendix 3).

Electrodes symmetrically placed within the borehole above and below the magnetic resonance device and oppositely polarized produce a current field predominately parallel to the borehole axis. Only that component of this axially directed current field external to the sensitive volume produces phase modulation and is measured. This permits separate estimates of the resistance caused by borehole effects within the magnetic resonance sensitive volume and the desired resistance of the formation external to the magnetic resonance sensitive volume. Self induction tends to distribute the axial current flow peripherally ("skin effect"), decreasing the participation of the invaded zone in this latter measurement.

Changes in phase modulation produced by altering these current flows can be used to provide estimates of spin-spin relaxation time $T_2$ or Bloch-Torrey bulk diffusion coefficient D (U.S. Pat. No. 5,212,447 to Paltiel; U.S. Pat. No. 5,565,775 to Stallmach) which correlate with various petrophysical parameters. (Appendix 4).

The total current $\bar{J}$ consists of $i_z$ parallel to the borehole and $i_\rho$ radial to the borehole, since $i_\theta=0$. By the Maxwell-Ampere equation (in cylindrical coordinates):

$$\nabla x \bar{H} = \bar{J}$$

Since $\dfrac{\delta h_\rho}{\delta \theta} \equiv \dfrac{\delta h_\theta}{\delta \theta} \equiv \dfrac{\delta h_z}{\delta \theta} \equiv 0$ by cylindrical symmetry.

then $i_\rho = -\dfrac{1}{\rho}\dfrac{\delta(\rho h_\theta)}{\delta z} \triangleq -G_z$ (Appendix 1)

$i_z = \dfrac{1}{\rho}\dfrac{\delta(\rho h_\theta)}{\delta \rho} \triangleq G_\rho$ (Appendix 1, 2)

and $0 = \dfrac{\delta h_\rho}{\delta z} - \dfrac{\delta h_z}{\delta \rho}$

Any $h_\rho$ or $h_z$ is inconsequential since $\bar{1}_\rho h_\rho + \bar{1}_\theta H_0 = \bar{1}_\theta H_0$ and $\bar{k} h_z + \bar{1}_\theta H_0 = \bar{1}_\theta H_0$ to first order. (Slichter, C. P., Principles of Magnetic Resonance, Third edition, Springer-Verlag, Berlin; 1989, eq 7.376, 7.377, p. 358).

If the frequency of the phase modulating current is a multiple of the Carr-Purcell interval, then the bulk diffusion D can be separated from the spin-spin relaxation $T_2$ by regression analysis. Further, when the phase modulation frequency $\Omega$ is much greater than the gradient strength G there is little loss of signal resulting from diffusion through the oscillating gradient. (Appendix 4). (U.S. Pat. No. 5,565,775 to Stallmach).

In the radial connection, the current component $i_\rho$, perpendicular to the magnetic resonance sensitive volume, produces a gradient $\bar{G}$ of the Zeeman Field $H_0$ in the z-direction. Periodically varying $i_\rho$ by applying a periodic voltage between the central coaxial electrode array placed around the magnetic resonance device in the borehole and the symmetrically placed electrodes placed in the borehole above and below the magnetic resonance device phase modulates the magnetic resonance echo. This is an effect dependent only on the frequency and strength of $i_\rho$ at, and directly perpendicular to, the sensitive volume of the magnetic resonance device as described more fully in applicant's U.S. Pat. No. 5,412,322 (Appendix 3). The measured radial current density, $i_\rho$, is perpendicular to the sensitive volume of the magnetic resonance device. This conduction path is strongly influenced by borehole and invaded zone resistivity, as distinguished from the more peripheral formation resistivity.

In the axial connection, any closed circumferential line integral within the cylindrical sensitive volume, but drawn about the borehole axis, defines a set of areas each of which includes the current flowing in both the borehole itself and the formation within the sensitive volume, as well as the current in the supply wire to the down-hole electrode. This adds to zero, in the quasi-static state, if no current flows outside of the sensitive volume. If however, current flows in the formation surrounding, and peripheral to, the magnetic resonance sensitive volume, this peripheral current then represents the difference between the current in the supply wire and the total current within the sensitive magnetic resonance volume, and, by Stokes Law, produces a magnetic field $h_\theta$ which can phase modulate the spins in the sensitive volume, separating the two current components internal and external to the sensitive volume. (Appendices 2 and 5).

Self-inductance in this longer axially distributed current path produces eddy currents resulting in a greater component of flow of current in the more peripheral formation, particularly at higher frequencies and higher conductivity. (Smythe, W. R., "Static and Dynamic Electricity", McGraw-Hill Book Company, New York 1950, Chapter XI).

Figure 10:
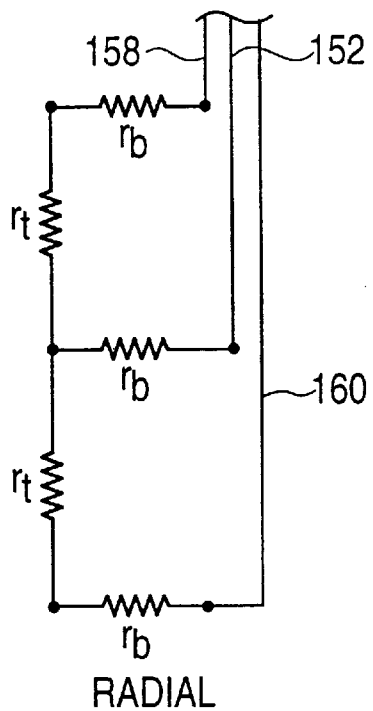
FIGS. 10 and 11 are schematic diagrams of the equivalent circuits at zero phase angle unity power factor series resonance of the apparatus of FIGS. 8 and 9, respectively.
Figure 11:
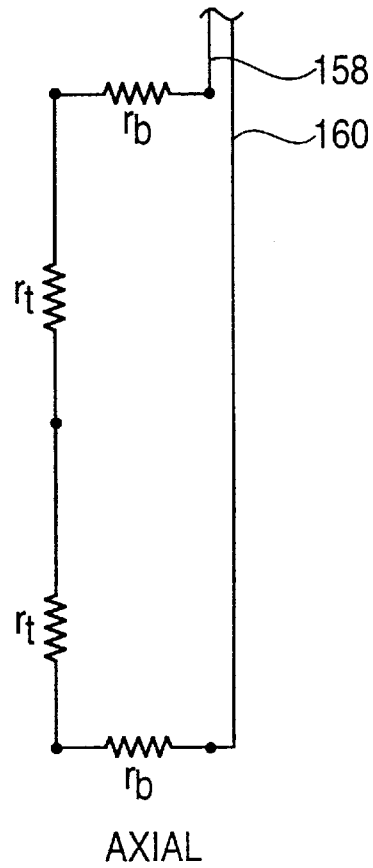

The two approximate equivalent circuits for the radial and axial modes of operation, at zero phase angle unity power factor series resonance, are shown in FIGS. 10 and 11, respectively, and are analyzed as follows:

a) In the radial case (FIG. 10):

$$r_{a_\rho} = (r_m + r_{mc} + r_{xo}) + (1/2)(r_t) + (1/2)(r_m + r_{mc} + r_{xo})$$

$$r_{a_\rho} = (1\ 1/2)r_b + (1/2)r_t$$

b) In the axial case (FIG. 11):

$$r_{a_k} = (r_m + r_{mc} + r_{xo}) + 2r_t + (r_m + r_{mc} + r_{xo})$$

$$r_{a_k} = 2r_b + 2r_t$$

where b, m, mc, xo, t and a pertain to borehole, mud, mudcake, invaded zone, formation, and apparent resistance, respectively.

Each resistance r is the ratio of the periodic voltage applied to the conducting formation and the axial, $i_z$, or radial, $i_\rho$, current as measured by detection of the amplitude of the sidebands in the magnetic resonance signal.

Solving for $r_t$:

$$r_t = (3/4)r_{ak} - r_{a\rho}$$

which is free of borehole and invaded zone effects.

For a non-conducting borehole, cylindrical electrodes of tool diameter of, for example, 6 inches, are preferably centered and stabilized in the borehole by a suitable structural component, such as a tool pad, a skid, an array of metal "bowstrings," or the like, which serve to increase the capacitive coupling, to center the tool in the borehole (reducing tool motion dephasing), and can provide electrical contact with the surrounding formation. The capacitance between a seven-foot long, six-inch diameter tool and any surrounding conducting formation near the sensitive volume can be expected to be very small, e.g. 20–200 micro micro Farads, assuming:

$$C = \frac{K}{18 \ln \frac{r_2}{r_1}} \times 10^{-9} \frac{Farad}{meter}$$

for a cylindrical capacitor, where K is the dielectric constant (about 2 for oil), $r_1$ is the radius of the electrode, and $r_2$ is the effective radius of the surrounding conducting formation. The capacitive reactance for oil at 1–10 KHz can be expected to be high, on the order of, for example, 0.008–6 megohms per electrode.

If the electrodes are connected to the secondary winding of an impedance matching transformer having a secondary to primary turns ratio "a," the secondary impedance will be reflected into the primary circuit divided by that ratio "$a^2$," reducing its magnitude. A primary loading inductance can then bring the entire circuit into zero phase angle unity power factor series resonance. This measures and cancels out the unknown capacitive reactances, leaving only the known equivalent circuit resistances of the wire line and transformer in series with the unknown total apparent formation resistance $r_a$.

The impedance matching transformer and most or all of the loading inductance can be made integral with the tool in the borehole, improving the power transmission efficiency of the wire line. The apparatus can be made partially tunable by a variable impedance at the wellhead to obtain zero phase angle unity power factor series resonance under varying tool environments.

Using two impedance matching circuits employing either a transformer or an autotransformer with variable impedances and separate metering in each current loop permits separate adjustment of each current loop to zero phase angle unity power factor series resonance. When the supply voltages and currents are equal, at series resonance, the tool is centered in the bed (U.S. Pat. No. 5,550,473 to Klein). The applied voltage less the known IR voltage drop through the known losses in the tool is the voltage applied to any conducting formation face opposing the tool electrodes.

The total current through the electrode array is measured at the wellhead. Phase modulation of the spins in the sensitive volume of the magnetic resonance device allows separation of this total current into two components; either into one component flowing axially through the borehole environment within the sensitive volume of the magnetic resonance device and another component flowing axially through the formation surrounding this sensitive volume (in the axial connection), or into one radial component perpendicular to the sensitive volume of the magnetic resonance device and another component flowing along, and in the proximity of, the borehole axis (in the radial connection).

Empirical determination of geometric factors permits estimation of formation resistivity $R_t$ peripheral to the tool and invaded zone resistivity $R_{xo}$ (if any) near the tool from the measured resistance $r_a$, in each case. See, Bassiouni, op. cit. p. 107–111.

The following steps will yield a measurement of total current and applied voltage at the conducting formation surface:

a) In the radial case:
1. Select $\hat{V}_u$ and $\hat{V}_L$ polarity for radial connection.
2. Select $\hat{Z}_u$ and $\hat{Z}_L$ for zero phase angle unity power factor.
3. Select $\hat{V}_u$ and $\hat{V}_L$ so that $$\hat{V}_L - \hat{V}_U = (\hat{I}_U + \hat{I}_L)\left(R_w + R_p + \frac{R_s}{a^2}\right)$$

then:

$$\hat{V}_p = a\left(\hat{V}_L - \hat{I}_L\left(2R_w + R_p + \frac{R_s}{a^2}\right) + \hat{I}_u R_w\right) \text{ or}$$

$$\hat{V}_p = a\left(\hat{V}_U + \hat{I}_U\left(2R_w + R_p + \frac{R_s}{a^2}\right) - \hat{I}_L R_w\right)$$

with $\hat{I}_\rho$ determined by the amplitude of the second sideband of the magnetic resonance signal (Appendix 3):

$$|V_\rho / I_\rho| \cong 1\tfrac{1}{2}r_b + \tfrac{1}{2}r_t \triangleq r_{a\rho}$$

b) In the axial case:
1. Adjust $\hat{Z}_u' = \hat{Z}_L'$ for borehole environment to set tuning range for $\hat{Z}_u$ and $\hat{Z}_L$.
2. Select $\hat{V}_u$ and $\hat{V}_L$ polarity for axial connection.
3. Adjust $\hat{V}_u$ and $\hat{V}_L$ for $\hat{I}_u = \hat{I}_L$ and $\hat{I}_N = 0$.
4. Tune with $\hat{Z}_u$ and $\hat{Z}_L$ for maximum $\hat{I}_u$ and $\hat{I}_L$ with zero phase angle and unity power factor.
5. Repeat 3 and 4 as needed.
   then, with $\hat{I}_u = \hat{I}_L \triangleq \hat{I}$:

$$\hat{V}_u + \hat{V}_L = \hat{I}\left(2R_w + 2R_p + \frac{2R_s}{a^2} + \frac{r_a}{a^2}\right)$$

the voltage applied at the conducting formation face is:

$$\hat{V}_t = a\left[(\hat{V}_u + \hat{V}_L) - 2\hat{I}\left(R_w + R_p + \frac{R_s}{a^2}\right)\right]$$

With $I_t$ determined by the amplitude of the first sideband of the magnetic resonance signal—(Appendix 3):

$$\left|\frac{V_t}{I_t}\right| = r_{bu} + r_{tu} + r_{tl} + r_{bl} \cong 2r_b + 2r_t \triangleq r_{ak}$$

The apparatus described herein permits estimation of formation resistivity $R_t$ and invaded zone resistivity $R_{xo}$ using experimentally determined empirical geometric factors relating measured resistance to resistivity.

The early short Tcp component of the CPMG sequence can be used to estimate the surface associated irreducible water saturation, free of clay effects, as the bound volume irreducible component (BVIRR) of total porosity (U.S. Pat. No. 5,557,200 to Coates).

The component of total porosity free of solid-liquid interface surface effects can be estimated from the amplitude of the magnetic resonance signal during the later long Tcp portion of the CPMG sequence. This component of total porosity contains spins from water and may contain spins from producible non-conducting hydrocarbons (U.S. Pat. No. 5,539,309 to Van Wyk).

The total porosity, excluding the water associated with high surface area shales or clays, is termed the effective porosity and can be estimated by regression analysis of a complete short Tcp CPMG echo train (1–3 ms) (U.S. Pat. No. 5,557,200 to Coates).

The relaxation time $T_r$ (or wait time W) may be adjusted to create $T_1$ saturation, or allow $T_1$ relaxation, of spins from natural gas, creating multiple selective CPMG echo trains that can be subtracted to estimate the presence of and a restricted diffusion coefficient of the gas (U.S. Pat. Nos. 5,497,087 and 5,498,960, both to Vinegar).

The amplitude or frequency of the applied phase-modulating current flux can be varied to permit estimation of the unrestricted bulk diffusion coefficient D or the intrinsic spin-spin relaxation $T_2$ of the bulk fluid that is free of surface effects (U.S. Pat. No. 5,565,775 to Stallmach). (Appendix 4).

The parameters of the sequences can be continuously altered to provide the optimum statistical reliability with the minimum logging time (U.S. Pat. No. 5,309,098 to Coates; No. 5,486,762 to Freedman; and No. 5,517,115 to Prammer).

The continuous efficient logging of $R_t$ and $R_{xo}$, together with the continuous measurement of the various components of porosity, the restricted and unrestricted diffusion coefficients, and the various $T_1$ and $T_2$ relaxation coefficients, permits graphical computation of the formation water resistance $R_w$. (Theory, Measurement and Interpretation of Well Logs; Bassiouni, Z.; SPE Textbook series, Volume 14, Richardson, Tex., 1994, p. 276); the single m-n exponent w for irreducible water saturation ($W_1$) and for water filled zones ($W_w$) (U.S. Pat. No. 5,412,320 to Coates); and of log $R_{xo}/R_t$ quick-look reconnaissance for zones with movable hydrocarbons (Bassiouni; op. cit., p. 252).

Numerous other combinations and permutations of functions of the data produced by the well logging tool will be apparent to the experienced well-log analyst, petrogeologist, and geophysicist.

Inasmuch as the present invention is subject to many variations, modifications and changes in detail, it is intended that all matter contained in the foregoing description, the attached appendices or the accompanying drawings shall be interpreted as illustrative and not in a limiting sense.

APPENDIX 1

Mathematical Relationship Between Applicant's U.S. Pat. No. 5,412,322 and The Present Invention Consider an orthogonal $\bar{i}$, $\bar{j}$, $\bar{k}$ rectilinear space x', y', z' bounded by $0 \leq x'$; $y' \leq 2r$; $-\infty < z' < +\infty$; with $\bar{i} \times \bar{j} = \bar{k}$ Transform this space to an orthogonal cylindrical system with circular symmetry $\theta$, $\rho$, Z such that $$dz' = \rho d\theta \quad \bar{i} \times \bar{j} = \bar{k}$$
$$dx' = d\rho \quad \bar{1}_\rho \times \bar{k} = \bar{1}_\theta$$
$$dy' = dz$$

The gradient $\bar{G}' \triangleq \nabla h_{z'}$. The Larmor frequency $\omega =$ $$\gamma\left(Ho + \int \bar{G}' \cdot d\bar{s}'\right); d\bar{s}' \triangleq = \bar{i}dx' + \bar{j}dy' + \bar{k}dz'$$

$$\rho \bar{G} \triangleq \nabla(\rho h_\theta);$$

$$\omega = \gamma\left(Ho + \int \bar{G} \cdot d\bar{s}\right); d\bar{s} = \bar{1}_\rho d\rho + \bar{k}dz + \bar{1}_\theta d\theta$$

$$i_{z'} \equiv \frac{\delta h_{x'}}{\delta z'} \equiv \frac{\delta h_{y'}}{\delta z'} \equiv \frac{\delta h_{z'}}{\delta z'} \equiv 0 \equiv \frac{\delta h_\theta}{\delta h_\theta} \equiv \frac{\delta h_\rho}{\delta \theta} \equiv \frac{\delta h_z}{\delta \theta} \equiv i_\theta$$

$$\bar{J}' \triangleq \bar{i}i_{x'} + \bar{j}i_{y'} + \bar{k}i_{z'}; \bar{J} \triangleq \bar{1}_\rho i_\rho + \bar{k}i_z + \bar{1}_\theta i_\theta$$

$$\bar{H}' \triangleq \bar{i}h_{x'} + \bar{j}h_{y'} + \bar{k}(Ho + h_{z'});$$

$$\bar{H} \triangleq \bar{1}_\rho h_\rho + \bar{K}h_z + \bar{1}_\theta(Ho + h_\theta)$$

$$\nabla \times \bar{H}' = \bar{i}\left(\frac{\delta h_{z'}}{\delta y'}\right) + \bar{j}\left(-\frac{\delta h_{z'}}{\delta x'}\right) + \bar{k}(0) = \bar{J}' \quad \text{(Maxwell-Ampere)}$$

$$\bar{k} \times (\bar{\nabla} \times \bar{H}') = \bar{i}\left(\frac{\delta h_{z'}}{\delta x'}\right) + \bar{j}\left(\frac{\delta h_{z'}}{\delta y'}\right) \equiv \nabla h_{z'} \triangleq \bar{G}'$$

$$\therefore \bar{K} \times \bar{J}' = \bar{G}'; |J'| = |G'| \quad q.e.d.$$

-continued $$\nabla \times \overline{H} = -\overline{1}_\rho \frac{1}{\rho} \frac{\delta(\rho h_\theta)}{\delta z} + \overline{1}_\theta(0) + \overline{k} \frac{1}{\rho} \frac{\delta(\rho h_\theta)}{\delta \rho} = \overline{J}$$

$$(\nabla \times \overline{H}) \times \rho \overline{1}_\theta = \overline{k} \frac{\delta(\rho h_\theta)}{\delta z} + \overline{1}_\rho \frac{\delta(\rho h_\theta)}{\delta \rho} \equiv \stackrel{\Delta}{=} (\rho h_\theta) \stackrel{\Delta}{=} \rho \overline{G}$$

$$\therefore \overline{J} \times \rho \overline{1}_\theta = \rho \overline{G}; |J| = |G| \quad q.e.d.$$

APPENDIX 2

Magnetic Field in the Axial Mode $$i_z = \frac{1}{\rho} \frac{\delta(\rho h_\theta)}{\delta \rho}; i_z \rho d\rho = d(\rho h_\theta)$$

$$\int_o^r i_z 2\pi \rho d\rho = 2\pi \int_o^{rh_\theta} d(\rho h_\theta)$$

$$I = 2\pi r h_\theta$$

$$h_\theta = \frac{I}{2\pi r}$$

which follows more directly from Stokes' Law.

APPENDIX 3

Frequency Spectrum and Relative Strength of Magnetic Resonance Signal

In SI units, $\omega = \gamma H$ with H in amperes/meter and $\gamma$ in meters/ampere-second. The Zeeman field $H_0$ creating precession about the $\overline{1}_\theta$ axis consists of a static portion $H_\theta$ created by the magnetic resonance tool permanent magnets and a superimposed oscillating field $h_\theta$ of frequency $\Omega$ created by the current flux J perpendicular to the Zeeman field $H_0$ (Wollin, U.S. Pat. No. 5,412,322).

Then:

$$H_o = H_\theta + h_\theta \cos \Omega t \quad \text{(Appendix 1)}$$

$$\overline{J} \times \frac{\overline{H}o}{Ho} = \overline{G} = \frac{1}{\rho} \nabla \rho h_\theta$$

a) In the radial connection:

$$dh_\theta = G_z dz = \frac{1}{\rho} \frac{\delta(\rho h_\theta)}{\delta z} dz = -i_\rho dz$$

$$h_\theta = -i_\rho z$$

$$2\pi r L i_\rho = I_\rho$$

$$h_\theta = -\frac{I_\rho}{2\pi r L} z$$

b) In the axial connection:

$$dh_\theta = G_\rho d\rho = \left(\frac{1}{\rho} \frac{\delta(\rho h_\theta)}{\delta \rho}\right) d\rho = i_z d\rho$$

for a constant radius cylinder r $$h_\theta = \frac{I_t}{2\pi r} \quad \text{(Appendix 2, 5)}$$

$I_t$ being the total axial current flowing within the cylinder boundary.

Since $\omega = \gamma H$,
then $\omega_0 = \gamma H_0 + \gamma h_\theta \cos \Omega t$
The phase acquired by each spin during time t is $$\Phi_o = \int_0^t \omega_0 dt = \gamma H_\theta t + \frac{\gamma h_\theta}{\Omega} \sin \Omega t$$

$$\Phi_o \stackrel{\Delta}{=} \omega_\theta t + u \sin \Omega t; u \stackrel{\Delta}{=} \frac{\gamma h_\theta}{\Omega}$$

In the sensitive volume of constant spin density containing a uniform magnetization of m spins per unit length, the total magnetization is:

$$\hat{M} = \int_{-L/2}^{+L/2} m e^{j\Phi} dz$$

Taking the Fourier transform with respect to time:

$$\mathcal{F}\hat{M} = \int_{-\infty}^{+\infty} \hat{M} e^{-j\omega t} dt = \int_{-L/2}^{+L/2} m \int_{-\infty}^{+\infty} e^{j(\Phi - \omega t)} dt dz$$

Defining $p = \frac{\omega_o - \omega}{\Omega}; u = \frac{\gamma h_\theta}{\Omega}; \phi = \Omega t$ yields $\mathcal{F}\hat{M} = \int_{-L/2}^{+L/2} m \left(\frac{1}{\Omega}\right) \oint_{complex} e^{j(p\phi - u\sin\phi)} d\phi dz$ by replacing $\phi$ with a complex variable and integrating in the complex plane. Then:

$$\mathcal{F}\hat{M} = \left(\frac{\pi}{\Omega}\right) \int_{-L/2}^{+L/2} m J_n(u) dz$$

for integral values of n. (Sommerfeld: Math. Ann. 47,335, 1896).

a) In the axial connection:

$$M = mL$$

$$u = \frac{\gamma}{\Omega} \cdot \frac{I_t}{2\pi r}$$

$$\mathcal{F}\hat{M} = M \frac{\pi}{\Omega} J_n\left(\frac{\gamma}{2\pi r \Omega} I_t\right)$$

where M is the total number of spins in the sensitive volume.

b) In the radial connection:

$$u = \frac{-\gamma}{\Omega} i_\rho z; 2\pi r L i_\rho = I_\rho; u = -\frac{\gamma}{\Omega} \frac{I_\rho}{2\pi r L} z$$

$$\mathcal{F}\hat{M} = M \cdot \frac{\pi}{\Omega} \cdot \frac{1}{L} \cdot \int_{-L/2}^{L/2} J_n\left(\frac{-\gamma I_\rho}{2\pi r L \Omega} z\right) dz$$

for n even only, since $J_n(u) = -J_n(-u)$ for n odd

Approximations

For small values of u:

$$J_n(u) \cong \frac{u^n}{n' 2^n}, \text{ and}$$

-continued $$J_o(u) \cong 1; \quad J_1(u) \cong \tfrac{1}{2}u; \quad J_2(u) \cong \tfrac{1}{8}u^2$$

a) In the axial connection:
For the first sideband $J_1(u)$ $$\mathcal{F}\hat{M} = M\frac{\gamma}{4r\Omega^2}I_t$$

b) In the radial connection:
For the second sideband $J_2(u)$ $$\mathcal{F}\hat{M} = M \cdot \frac{\pi}{\Omega L} \cdot \frac{1}{8} \cdot \left(\frac{-\gamma I_\rho}{2\pi r L \Omega}\right)^2 \cdot \frac{L^3}{12}$$

$$= M \cdot \frac{1}{384\pi r^2} \cdot \frac{\gamma^2}{\Omega^3} \cdot I_\rho^2$$

$\gamma = 34\pi^2$ meters/amp-seconds for protons.

The strength of the sidebands $J_1(u)$ and $J_2(u)$ relative to the central Larmor frequency $J_0(u)$, for small values of the argument u, is:

a) In the axial connection:

$$\frac{\mathcal{F}\hat{M}_1}{\mathcal{F}\hat{M}_o} = \tfrac{1}{2}u = \frac{1}{4\pi r} \cdot \frac{\gamma I_t}{\Omega} \cong \frac{1}{4\pi(.2)} \cdot \frac{34\pi^2 I_t}{2\pi f_p} \cong 21.2\frac{I_t}{f_p}$$

for $f_p = 10^4$ Hz, $\dfrac{\mathcal{F}_1}{\mathcal{F}_o} = 21.2 \times 10^{-4} I_t$ b) In the radial connection:

$$\frac{\mathcal{F}\hat{M}_2}{\mathcal{F}\hat{M}_o} = \frac{\tfrac{1}{8}\left(\frac{-\gamma I_\rho}{2\pi r L \Omega}\right)^2 \cdot \frac{L^3}{12}}{L} = \frac{1}{8(2\pi r)^2(12)} \cdot \left(\frac{\gamma I_\rho}{\Omega}\right)^2$$

$$= \frac{1}{15.4\pi^2} \cdot \left(\frac{\gamma I_\rho}{\Omega}\right)^2 = \frac{1}{15.4\pi^2}\cdot\left(\frac{34\pi^2}{2\pi}\right)^2\cdot\left(\frac{I_\rho}{f_p}\right)^2$$

$$= \frac{(17)^2}{15.4}\cdot\left(\frac{I_\rho}{f_p}\right)^2 \cong 18.8\left(\frac{I_\rho}{f_p}\right)^2$$

for $f_p = 10^4$ Hz, $\dfrac{\mathcal{F}_2}{\mathcal{F}_0} = 188 \times 10^{-9} I_\rho^2$

APPENDIX 4

Bloch-Torrey Bulk Diffusion—(Periodic Gradient)

$$\frac{d\hat{M}}{dt} = -\frac{\hat{M}}{T_2} - j\hat{M}\gamma Gz\sin\Omega t + D\nabla^2\hat{M}$$

Let $\hat{M} = M_o e^{-t/T_2} e^{+\frac{j\gamma Gz\cos\Omega t}{\Omega}} A_t$ $$\frac{1}{A}\delta\frac{A}{\delta t} = D\left(j\frac{\gamma G}{\Omega}\cos\Omega t\right)^2 = -D\left(\frac{\gamma G}{\Omega}\right)^2\cos^2\Omega t$$

$$\ln A = -D\left(\frac{\gamma G}{\Omega}\right)^2\int\cos^2\Omega t\, dt = -D\left(\frac{\gamma G}{\Omega}\right)^2\left(\frac{t}{2}+\frac{\sin 2\Omega t}{4\Omega}\right)$$

Burington, R. S.; Handbook of Mathematical Tables and Formulas; Handbook Publishers, Inc. Sandusky, Ohio, 1949.

$$\hat{M} = M_o e^{j\frac{\gamma G}{\Omega}z\cos\Omega t}\left[e^{-\frac{t}{T_2}}e^{-D\left(\frac{\gamma G}{\Omega}\right)^2\left(t/2 + \frac{\sin 2\Omega t}{4\Omega}\right)}\right]$$

when $t = 2\tau$ the phase terms $e^{j+}$ and $e^{j-}$ cancel.

If $\Omega = n\dfrac{\pi}{4\tau}$, for $n$ odd, then $\sin 2\Omega(2\tau) = 0$ and $\cos\Omega(2\tau) = 0$.

Then $\hat{M} = M_o e^{-2\tau\left[1/T_2 + \tfrac{1}{2}D\left(\frac{\gamma G}{\Omega}\right)^2\right]}$ or $\ln\hat{M} = \ln M_o - 2\tau\left(\dfrac{1}{T_2}\right) - \left[\tau\left(\dfrac{\gamma G}{\Omega}\right)^2\right](D)$ After Slichter, C. P. "Principles of Magnetic Resonance" Springer-Verlag, 3rd Edition, 1989, Appendix G, $\gamma$ and $M_0$ are constants in each experiment. G, $\Omega$ and $\tau$ are operator adjustable. D and $T_2$ are to be measured. $|G|=|J|$; $\tau=\tau$ Carr-Purcell; $\Omega = 2\pi f_p$ ($f_p$ is the frequency of J).

APPENDIX 5

Analysis of the Axial Circuit

Consider a closed line integral in the $1_\theta$ direction through the cylindrical circular sensitive volume of radius $\rho$ of the magnetic resonance logging tool; wherein the Zeeman Field is of magnitude $H_0 = H_\theta + h_\theta$ with $\omega_0 = \gamma H_\theta$ being the central frequency of the narrow band $H_1$ radio frequency excitation field. Then, in the quasi-static state, Stokes Law yields $$\oint \bar{H}\cdot d\bar{s} = \iint(\bar{\nabla}\times\bar{H})\cdot d\bar{a}.\text{ But }\bar{\nabla}\times\bar{H} = \bar{\imath}$$

$$2\pi\rho h_\theta = \iint \bar{\imath}\cdot d\bar{a} = I_s - (Im + Imc + Ixo)$$

and It=Is−(Im+Imc+Ixo) since $\bar{\nabla}\cdot\bar{\imath}=0$ and Is and (Im+Imc+Ixo) are in opposite directions. The formation resistance $$r_t = \frac{V_s}{I_t} = \frac{V_s}{2\pi\rho h_\theta}$$

where $I_t$ is measured from its effect on phase modulation and $V_s$ is the adjustable known supply voltage applied at the formation.

Here s refers to total supply electrode voltages and currents, m refers to mud, mc refers to mudcake, xo refers to transition zone, and t refers to the formation of interest surrounding the sensitive volume of the magnetic resonance well logging device.

Therefore, only current flowing axially but peripheral to the sensitive volume will produce phase modulation of the spins within the sensitive volume.

Further, whatever radial components of the total current traverse the sensitive volume do so in symmetrically opposite fields above and below the trans-axial plane of symmetry of the sensitive volume and produce $h_\theta$ fields that cancel.

APPENDIX 6

SIGNAL TO NOISE RATIO

Each sideband element is equally broadened by dephasing caused by static variations in the ambient Ho field, and is periodically rephased by the CPMG $\pi$ pulse. Each sideband element can be represented by a pulse in the frequency domain, or by a "sync" function in the time domain as illustrated in FIG. 13b.

The noise power limiting the estimation of each sideband signal strength $P_n$ is:

$$P_n = K\tau \Delta f$$

$$\Delta f = \frac{1}{T}$$

where K is Boltzman's constant, $\tau$ is the ambient temperature at the signal generator (the formation), $R_O$ is the characteristic impedance of the transmission line, and $\Delta f$ is the bandwidth of each sideband element, which element width is the same throughout the line spectrum.

Each sideband envelope can be written as:

$$V_{(t)} = \hat{V} \frac{T}{\pi} \cdot \frac{\sin\left(\frac{\pi}{T}t\right)}{t}$$

where $\hat{V}$ is a peak voltage set by the spin density, the sideband frequency (approximately the Larmor $J_0(\ )$ frequency), and by system geometry; and 2T is the width of the central lobe of the "sync" function. The Fourier transform $F(\omega)$ of $V(t)$ is:

$$F(\omega) = \hat{V} T P_{\pi/T}(\omega)$$

where $P_{\pi/T}(\omega)$ is a pulse function of width $$\frac{2\pi}{T}.$$

By the Parseval-Bessel Theorem, the total energy $E_s$ of $V_{(t)}$ is:

$$E_s = \frac{\hat{V}^2 T}{4R_o}$$

If this energy $E_s$ is assumed to lie almost entirely within the main central lobe of the "sync" function, the average signal power can be estimated as:

$$P_s \cong \frac{E_s}{2T} = \frac{\hat{V}^2}{8R_o}$$

Then, the signal-to-noise power ratio is:

$$\frac{P_s}{P_n} = \hat{V}^2 T \cdot \frac{1}{8K\tau R_o}$$

For an ambient temperature of 400° Kelvin, in a 50 ohm line:

$$\frac{P_s}{P_n} = \hat{V}^2 T \frac{1}{8(1.38 \times 10^{-23})(400)(50)} = \hat{V}^2 T(.453 \times 10^{18})$$

For a 4 ms pulse, $T = 2 \times 10^{-3}$ $$\frac{P_s}{P_n} = \hat{V}^2 (9.06 \times 10^{14})$$

or $$\hat{V} = \left(\frac{P_s}{P_n}\right)^{1/2} (0.333 \times 10^{-7})$$

For $\frac{P_s}{P_n} = 100$, $\hat{V} \cong 0.3 \mu V$; 20 dB signal/noise

For $\frac{P_s}{P_n} = 10$, $\hat{V} \cong 0.1 \mu V$; 10 dB signal/noise.

What is claimed is:

1. A method for estimating resistivity in a formation surrounding a borehole, comprising:
   providing a magnetic resonance well logging tool with a Faraday shield;
   placing said magnetic resonance well logging tool and Faraday shield in the borehole and capacitively coupling the same with the formation surrounding the borehole;
   energizing the formation surrounding the borehole;
   selectively applying phase modulating voltages to said Faraday shield and an upper and a lower coupling member to establish current fields in axial and radial directions, respectively, in the formation surrounding the borehole; and
   measuring the current strength and distribution of said current fields by detecting phase modulation of spins of materials in a sensitive volume.

2. The method of claim 1, further comprising providing a supply and processing circuitry.

3. The method of claim 2, wherein the supply and processing circuitry comprises at least one of a phase modulating power supply or a processor and recorder.

4. The method of claim 1, further comprising providing a receiving and transmitting circuitry.

5. The method of claim 4, wherein the receiving and transmitting circuitry comprises at least one of a telemetry circuit, a pulse programmer, a computer, an analog-to-digital converter, a variable frequency RF source, a sideband detector, an RF driver, a phase shifter, a receiver, an RF power amplifier, a receiver pre-amplifier, or a transmitter/receiver matching circuit.

6. A method for determining resistivity in a formation surrounding a borehole, comprising:
   capacitively coupling a phase-modulating current to said formation by placing first, second, and third spaced coupling members in the borehole and selectively applying low frequency power signals to the first and second coupling members and to the second and third coupling members, respectively;
   placing a magnetic resonance well logging tool in the borehole in proximity to the second coupling member to produce a magnetic resonance sensitive volume around said tool; and
   detecting phase modulation of spins in said sensitive volume to derive data representative of the resistivity of materials in said formation.

7. The method of claim 6, wherein the first, second, and third spaced coupling members are suspended in a spaced relationship on a cable.

8. A method for determining resistivity in a formation surrounding a borehole, comprising:
   placing capacitive coupling members above and below a center capacitive coupling member containing a magnetic resonance well logging tool;
   selectively establishing current fields in axial and radial directions, respectively, in a sensitive region around the tool; and
   determining resistivity in the sensitive region around the tool utilizing the current fields in axial and radial directions.

9. The method of claim 8, wherein selectively establishing current fields comprises utilizing a phase modulating power supply including a polarity reversing switch which is coupled to both of the capacitive coupling members through respective matching inductances.

10. The method of claim 8, wherein selectively establishing current fields comprises providing similar polarization to both of the capacitive coupling members.

11. The method of claim 8, wherein selectively establishing current fields comprises providing opposite polarization to each of the capacitive coupling members.

12. A method for determining resistivity in a formation surrounding a borehole, comprising:

placing a magnetic resonance well logging tool in said borehole and energizing said tool to produce a magnetic resonance sensitive volume thereabout;

selectively measuring current flow in said formation both perpendicular to and parallel to the borehole axis within and adjacent to said sensitive volume; and determining resistivity in said formation utilizing said current flow measured perpendicular to and parallel to the borehole axis.

13. The method of claim 12, wherein placing said magnetic resonance well logging tool in a borehole comprises placing said magnetic resonance well logging tool in a conducting borehole.

14. The method of claim 12, wherein placing said magnetic resonance well logging tool in a borehole comprises placing said magnetic resonance well logging tool in a non-conducting borehole.

15. The method of claim 14, further comprising capacitively coupling Very Low Frequency currents to the formation through impedance matching circuits.

16. A method for determining resistivity in a formation surrounding a borehole, comprising:

placing a magnetic resonance well logging tool having a Faraday shield in the borehole and capacitively coupling the same with the formation surrounding the borehole;

placing upper and lower coupling members in the borehole above and below the Faraday shield of said magnetic resonance well logging tool, respectively, and capacitively coupling the same with the formation surrounding the borehole; and selectively applying voltages to said Faraday shield and said upper and lower coupling members to establish current fields in axial and radial directions, respectively, in the formation; and measuring the resulting nuclear magnetic resonance signals to determine resistivity within the formation.

17. A method for measuring diffusion coefficient and spin relaxation time in a nuclear magnetic resonance well logging system, comprising:

placing a nuclear magnetic resonance well logging device in a borehole having a surrounding formation;

energizing the nuclear magnetic resonance well logging device to generate a phase modulating current at a selected frequency and with a predetermined magnetic resonance pulse interval;

varying the intensity of the phase modulating current and the frequency and magnetic resonance pulse interval so as to change the amplitude of a magnetic resonance signal; and determining a value for diffusion coefficient and a value for spin relaxation time utilizing the magnetic resonance signal.

18. The method of claim 17, wherein placing said nuclear magnetic resonance well logging device in a borehole having a surrounding formation comprises placing said nuclear magnetic resonance well logging device in a conducting borehole having a surrounding formation.

19. The method of claim 17, wherein placing said nuclear magnetic resonance well logging device in a borehole having a surrounding formation comprises placing said nuclear magnetic resonance well logging device in a non-conducting borehole having a surrounding formation.

20. A method for estimating resistivity in a formation surrounding a borehole, comprising:

providing a magnetic resonance well logging tool with a Faraday shield;

placing said magnetic resonance well logging tool and Faraday shield in the borehole and capacitively coupling the same with the formation surrounding the borehole;

energizing the formation surrounding the borehole;

selectively applying phase modulating voltages to said Faraday shield and an upper and a lower coupling member to establish current fields in at least one of axial and radial directions in the formation surrounding the borehole; and measuring the current strength and distribution of said current fields by detecting phase modulation of spins of materials in a sensitive volume.

21. A method for determining resistivity in a formation surrounding a borehole, comprising:

placing capacitive coupling members above and below a center capacitive coupling member containing a magnetic resonance well logging tool;

selectively establishing current fields in at least one of axial and radial directions in a sensitive region around the tool; and determining resistivity in the sensitive region around the tool utilizing the current fields.

22. A method for determining resistivity in a formation surrounding a borehole, comprising:

placing a magnetic resonance well logging tool in said borehole and energizing said tool to produce a magnetic resonance sensitive volume thereabout;

selectively measuring current flow in said formation, the current flow being at least one of perpendicular to and parallel to the borehole axis, within and adjacent to said sensitive volume; and determining resistivity in said formation utilizing said current flow which is measured.

23. A method for determining resistivity in a formation surrounding a borehole, comprising:

placing a magnetic resonance well logging tool having a Faraday shield in the borehole and capacitively coupling the same with the formation surrounding the borehole;

placing upper and lower coupling members in the borehole above and below the Faraday shield of said magnetic resonance well logging tool, respectively, and capacitively coupling the same with the formation surrounding the borehole; and selectively applying voltages to said Faraday shield and said upper and lower coupling members to establish current fields in at least one of axial and radial directions in the formation; and measuring the resulting nuclear magnetic resonance signals to determine resistivity within the formation.

* * * * *